United States Patent [19]
Knifton et al.

[11] Patent Number: 5,939,592
[45] Date of Patent: Aug. 17, 1999

[54] METHODS FOR DECOMPOSING ESTERS AND PURIFYING ALCOHOLS

[75] Inventors: John Frederick Knifton, Houston; John Ronald Sanderson, Austin; William Alan Smith, Round Rock, all of Tex.

[73] Assignee: Huntsman Specialty Chemicals Corp., Austin, Tex.

[21] Appl. No.: 08/966,879

[22] Filed: Nov. 10, 1997

Related U.S. Application Data

[63] Continuation-in-part of application No. 08/727,718, Oct. 7, 1996, abandoned.

[51] Int. Cl.$^6$ .............................. C07C 27/02; B01J 23/40
[52] U.S. Cl. ................ 568/877; 502/326; 568/909.8; 568/913; 568/922
[58] Field of Search ................ 568/909.8, 913, 568/922, 877; 502/326

[56] References Cited

U.S. PATENT DOCUMENTS

| | | | |
|---|---|---|---|
| 4,296,263 | 10/1981 | Worrell | 568/910 |
| 4,547,598 | 10/1985 | Sanderson et al. | 568/922 |
| 4,704,482 | 11/1987 | Sanderson et al. | 568/922 |
| 4,705,903 | 11/1987 | Sanderson et al. | 568/922 |
| 4,742,179 | 5/1988 | Sanderson et al. | 568/913 |
| 4,873,380 | 10/1989 | Sanderson et al. | 568/914 |
| 4,910,349 | 3/1990 | Sanderson et al. | 568/909.8 |
| 4,912,266 | 3/1990 | Sanderson et al. | 568/909.8 |
| 4,912,267 | 3/1990 | Sanderson et al. | 568/909.8 |
| 4,922,033 | 5/1990 | Sanderson et al. | 568/909.8 |
| 4,922,034 | 5/1990 | Sanderson et al. | 568/909.8 |
| 5,185,480 | 2/1993 | Sanderson et al. | 568/913 |
| 5,243,091 | 9/1993 | Kruse et al. | 568/697 |
| 5,292,964 | 3/1994 | Gupta | 568/697 |
| 5,354,912 | 10/1994 | Hwan et al. | 568/697 |
| 5,354,917 | 10/1994 | Sanderson et al. | 568/909.8 |
| 5,364,981 | 11/1994 | Knifton et al. | 568/698 |
| 5,386,065 | 1/1995 | Kruse et al. | 568/698 |
| 5,387,721 | 2/1995 | Kruse et al. | 568/697 |
| 5,395,982 | 3/1995 | Cassata et al. | 568/699 |

OTHER PUBLICATIONS

U.S. Application Ser. No. 08/727,718 filed Oct. 7, 1996.
Ponec and Bond, *Catalysis by Metals and Alloys,* pp. 520–524; Elsevier: Amsterdam (1995).

*Primary Examiner*—Alan L. Rotman
*Assistant Examiner*—Charanjit S. Aulakh
*Attorney, Agent, or Firm*—Arnold, White & Durkee

[57] ABSTRACT

A tertiary butyl alcohol charge stock typically contaminated with from about 0.5 to about 2 wt. % of formates and peroxides, is passed through an oxygenates decomposition reactor containing a bed of a decomposition catalyst comprising rhodium, platinum, palladium or mixture thereof at a temperature of from about 100 to about 280° C. to decompose the peroxides and formates, and to dehydrate a portion of the tertiary butyl alcohol to form isobutylene and water to thereby form a non-corrosive tertiary butyl alcohol feedstock that is substantially free from formates that is suitable for reaction with methanol in a methyl tertiary butyl ether etherification reactor to form a non-corrosive methyl tertiary butyl ether etherification reaction product from which methyl tertiary butyl ether can be recovered.

40 Claims, 2 Drawing Sheets

METHODS FOR DECOMPOSING ESTERS AND PURIFYING ALCOHOLS

The present application is a continuation-in-part of co-pending U.S. patent application Ser. No. 08/727,718 filed Oct. 7, 1996, now abandoned. The entire text of the above-referenced disclosure is specifically incorporated by reference herein without disclaimer.

BACKGROUND OF THE INVENTION

1. Field of the Invention

This invention relates to the decomposition of formate esters and the purification of alcohols, such as tertiary butyl alcohol for use in the manufacture of methyl tertiary butyl ether. More particularly, this invention relates to a method for the substantially complete removal of formate impurities, including tertiary butyl formate, from tertiary butyl alcohol to be used in the manufacture of methyl tertiary butyl ether from tertiary butyl alcohol and methanol.

Methyl tert-butyl ether is useful as a blending component in high octane gasoline.

2. Description of Related Art

Worrell U.S. Pat. No. 4,296,263 discloses the oxidation of isobutane with air to provide to tertiary butyl alcohol and tertiary butyl hydroperoxide. It is disclosed that the reaction product, a solution of tertiary butyl hydroperoxide in tertiary butyl alcohol contains minor amounts of oxygen-containing by-products such as acetic acid, formic acid and esters thereof that are purged from the system during purification of the reaction product.

The tertiary butyl hydroperoxide in the solution of tertiary butyl hydroperoxide in tertiary butyl alcohol can be decomposed thermally or catalytically to form additional tertiary butyl alcohol.

A number of catalysts have been proposed for this purpose, such as cobalt borate as disclosed in U.S. Pat. No. 4,547,598, a nickel, copper, chromia catalyst as disclosed in Sanderson et al. U.S. Pat. No. 4,704,482, an iron, copper, chromia, cobalt catalyst as disclosed in Sanderson et al. U.S. Pat. No. 4,705,903, a base treated hydrogenation catalyst from groups VIB or VIIIB of the Periodic Table as disclosed in Sanderson et al. U.S. Pat. No. 4,742,179, a nickel, copper, chromium and barium catalyst as disclosed in Sanderson et al. U.S. Pat. No. 4,873,380, a metal phthalocyanine catalyst as disclosed in Sanderson et al. U.S. Pat. No. 4,910,349, an imidazole-promoted methyl metal phthalocyanine catalyst as disclosed in Sanderson et al. U.S. Pat. No. 4,912,266, a base promoted metal phthalocyanine catalyst as disclosed in Sanderson et al. U.S. Pat. No. 4,912,267, a solid ruthenium catalyst as disclosed in Sanderson et al. U.S. Pat. No. 4,922,033, a promoted metal porphine catalyst as disclosed in Sanderson et al. U.S. Pat. No. 4,922,034, etc.

The tertiary butyl alcohol charge stock derived from tertiary butyl hydroperoxide is in this manner will be contaminated with oxygen-containing impurities.

Processes for the manufacture of methyl tertiary butyl ether from tertiary butyl alcohol and methanol are known, as illustrated, for example, by Kruse et al. U.S. Pat. No. 5,243,091, Gupta U.S. Pat. No. 5,292,964, Hwan et al. U.S. Pat. No. 5,354,912, Kruse et al. U.S. Pat. No. 5,386,065, Kruse et al. U.S. Pat. No. 5,387,721 and Cassata et al. U.S. Pat. No. 5,395,982. In the practice of these processes, the tertiary butyl alcohol feedstock is passed through a peroxides decomposition reactor before being charged to an etherification reactor together with methanol for the formation of methyl tertiary butyl ether.

For example, Kruse et al. U.S. Pat. No. 5,243,091 discloses a method for the preparation of methyl tertiary butyl ether wherein the tertiary butyl alcohol is initially charged to a peroxides decomposition zone, which is typically a thermal decomposition zone. When the peroxides are to be thermally decomposed, the peroxides-contaminated tertiary butyl alcohol feedstock is conventionally passed through a peroxides decomposition reactor at a temperature of about 100° C. to about 200° C., a pressure of about 80 to about 500 psia at a flow rate of about 0.5 to 20 volumes of feedstock per reactor volume per hour to thereby provide a substantially peroxides-free tertiary butyl alcohol reaction product. The thus-treated tertiary butyl alcohol, which will still contain oxygen-containing impurities such as tertiary butyl formate, is then mixed with methanol and the mixture is catalytically reacted to form an etherification reaction product comprising unreacted methanol, unreacted tertiary butyl alcohol, water, isobutylene, methyl tertiary butyl ether, and oxygen-containing impurities present in the tertiary butyl alcohol feedstock. Methyl tertiary butyl ether is recovered from the reaction mixture.

Sanderson et al. U.S. Pat. No. 5,354,917 discloses a method wherein an isobutane oxidation product comprising a solution of 5 to 30 wt. % of tertiary butyl hydroperoxide in tertiary butyl alcohol is brought into contact with a catalyst consisting of alumina or carbon having rhodium deposited thereon in order to convert the tertiary butyl hydroperoxide to decomposition products, principally tertiary butyl alcohol. Sanderson et al. specify reaction conditions including a temperature of about 25° C. to about 250° C. and a pressure of about 0 to 1000 psig, with a temperature of about 40° C. to about 150° C. and a pressure of about 0 psig being preferred. Tertiary butyl alcohol is recovered from the decomposition products but will be contaminated with minor amounts of oxygen-containing impurities including peroxides and formates. As a consequence, if a tertiary butyl alcohol feedstock prepared by the Sanderson et al. process is to be used in the preparation of methyl tertiary butyl ether, the feedstock must be treated in a preliminary peroxides decomposition zone for the decomposition of the peroxide impurities.

A variety of other catalysts may be used to treat a tertiary butyl alcohol feedstock contaminated with peroxide impurities, such as cobalt borate as disclosed in U.S. Pat. No. 4,547,598, a nickel, copper, chromia catalyst as disclosed in Sanderson et al. U.S. Pat. No. 4,704,482, an iron, copper, chromia, cobalt catalyst as disclosed in Sanderson et al. U.S. Pat. No. 4,705,903, a base treated hydrogenation catalyst from groups VIB or VIIIB of the Periodic Table as disclosed in Sanderson et al. U.S. Pat. No. 4,742,179, a nickel, copper, chromium and barium catalyst as disclosed in Sanderson et al. U.S. Pat. No. 4,873,380, a metal phthalocyanine catalyst as disclosed in Sanderson et al. U.S. Pat. No. 4,910,349, an imidazole-promoted methyl metal phthalocyanine catalyst as disclosed in Sanderson et al. U.S. Pat. No. 4,912,266, a base promoted metal phthalocyanine catalyst as disclosed in Sanderson et al. U.S. Pat. No. 4,912,267, a solid ruthenium catalyst as disclosed in Sanderson et al. U.S. Pat. No. 4,922,033, a promoted metal porphine catalyst as disclosed in Sanderson et al. U.S. Pat. No. 4,922,034, etc.

SUMMARY OF THE INVENTION

When tertiary butyl alcohol is prepared by the oxidation of isobutane and/or tertiary butyl hydroperoxide the tertiary butyl alcohol reaction product will contain minor amounts of contaminants such as tertiary butyl hydroperoxide, ditertiary butyl peroxide, allyl tertiary butyl peroxide, etc., and will typically also contain minor amounts of other oxygen-containing contaminants including acetone, isopropyl alcohol, dimethyl ether, etc., and acidic by-products such as acetic acid, formic acid and esters thereof, including methyl formate and tertiary butyl formate. The contaminated tertiary butyl alcohol charge stock prepared in this fashion is conventionally passed through a peroxides decomposition reactor to prepare a tertiary butyl alcohol feedstock that is fed to a methyl tertiary butyl ether etherification reactor together with methanol to provide a methyl tertiary butyl ether etherification product substantially free from peroxide impurities. The thus-treated tertiary butyl alcohol will still contain a minor amount of oxygen-containing impurities, such as acetone, isopropyl alcohol and dimethyl ether and also formate esters such as methyl formate and tertiary butyl formate. Tertiary butyl formate is removed only with great difficulty. Thereafter, during the reaction of tertiary butyl alcohol with methanol to form a reaction product containing methyl tertiary butyl ether and during the work-up of the reaction product, the oxygen-containing impurities, and especially the formate esters can decompose to form by-products including corrosive acidic by-products such as formic acid, thus creating a severe corrosion problem. The disclosed catalyst decomposes, among other things, formates and peroxides. Some other oxygen-containing impurities such as acetic acid and acetone, may not be decomposed by this catalyst.

These and other related problems are resolved through the process of the disclosed method wherein a tertiary butyl alcohol charge stock contaminated with from about 0.1 to about 10 wt. % of formate and peroxide impurities, is passed through an oxygenates decomposition reactor containing a bed of a decomposition catalyst (selected from at least one of rhodium, palladium, platinum, or mixtures thereof) at a temperature of about 100° C. to about 280° C. to decompose the peroxides and formate impurities, and to form a tertiary butyl alcohol feedstock substantially free from such impurities as evidenced by the low tertiary butyl formate content of the reaction product, for example, in the range of about 0.01 to about 0.1 wt. % of tertiary butyl formate. A significant portion of the tertiary butyl alcohol may be dehydrated in the oxygenates reactor to form isobutylene. This does not present a problem because isobutylene also reacts with methanol to form methyl tertiary butyl ether. Accordingly, the thus-prepared non-corrosive tertiary butyl alcohol feedstock having a tertiary butyl formate content of 0.1 wt. % or less and a titratable acidity of 3.0 KOH/g or less is suitable for reaction with methanol in a methyl tertiary butyl ether etherification reactor to form a non-corrosive methyl tertiary butyl ether etherification reaction product from which methyl tertiary butyl ether can be recovered.

Therefore, in respect this invention is a process for decomposing esters including contacting one or more esters with a catalyst including at least one of rhodium, platinum, palladium or a mixture thereof under conditions such that the esters are decomposed. Typically, the esters include one or more tormate esters, and most typically the esters are present in a contaminated alcohol mixture, although they may be present in other medium, typically in other liquid hydrocarbons. Contacting typically includes contacting the contaminated alcohol mixture with the catalyst. Advantageously, the contaminated alcohol mixture may further include one or more peroxides, and the contacting may further include contacting the alcohol mixture with the catalyst under conditions such that the peroxides are decomposed simultaneously, or in addition to, the esters. Typically, the contacting occurs at a temperature of from about 100° C. to about 280° C., and at a pressure of from about 0 to about 1000 psia, although any other suitable conditions may be employed. In one embodiment, the catalyst includes a support having from about 0.01 wt. % to about 10 wt. % of platinum deposited thereon; and the support includes at least one of alumina, silica alumina, titania, zirconia, silica, nickel, carbon, or a mixture thereof. In another embodiment, the catalyst includes a support having from about 0.01 wt. % to about 10 wt. % of palladium deposited thereon; and the support includes at least one of alumina, silica alumina, titania, zirconia, silica, nickel, carbon, or a mixture thereof. In still another embodiment, the catalyst includes a support having from about 0.01 wt. % to about 10 wt. % of rhodium deposited thereon; and the support includes at least one of alumina, silica alumina, titania, zirconia, silica, nickel, carbon, or a mixture thereof. In one embodiment, the catalyst may also be a pre-reduced catalyst, and the contacting further include contacting the one or more esters with the catalyst in the presence of hydrogen.

In another respect, this invention is a process for removing formate ester impurities from a contaminated alcohol mixture to form a purified alcohol mixture, including contacting the contaminated alcohol mixture with a catalyst material including at least one of rhodium, platinum, palladium, or a mixture thereof under conditions such that the formate ester impurities are decomposed and the alcohol mixture purified. Typically, the contaminated alcohol mixture includes a tertiary butyl alcohol, although the mixture may include other alcohols or mixtures thereof. Advantageously the contaminated alcohol mixture may further include one or more peroxides, and the contacting may further include contacting the alcohol mixture with the catalyst under conditions such that the peroxides are decomposed simultaneously, or in addition to, the formate ester impurities. In one embodiment, the catalyst material may be pre-reduced, and the contacting further include contacting the contaminated alcohol mixture with the catalyst material in the presence of hydrogen. In another embodiment, the contaminated alcohol mixture may include from about 0.1 wt. % to about 5 wt. % of formate ester impurities. In another embodiment, the formate ester impurities may include tertiary butyl formate, and the purified alcohol mixture may have a tertiary butyl formate content of about 0.1 wt. % or less, although a tertiary butyl formate content of about 0.2 wt. % or less, or a tertiary butyl formate content of about 0.3 wt. % or less, are also possible. In yet still another embodiment, the purified alcohol mixture may have a titratable acidity of about 3.0 mg KOH/g or less, and in another embodiment, may have a titratable acidity of about 1.5 mg KOH/g or less. Typically, greater than about 50% of the formate ester impurities are decomposed, although benefits may be realized when less than about 50% of the formate ester impurities are decomposed. In one embodiment, the catalyst includes palladium, and greater than about 90% of the formate ester impurities are typically removed from the contaminated alcohol mixture. In another embodiment the catalyst includes palladium, and is effective to remove greater than about 50% of the formate ester impurities from the contaminated alcohol mixture over a period of greater than about 3000 hours. In yet another embodiment, the catalyst includes an alumina or carbon support having from about 0.1 wt. % to about 5 wt. % of platinum deposited thereon. In another embodiment, the catalyst includes an alumina or carbon support having from about 0.1 wt. % to about 5 wt. % of palladium deposited thereon. In another embodiment, the catalyst includes an alumina or carbon support having from about 0.1 wt. % to about 5 wt. % of rhodium deposited thereon. The palladium catalyst may have a form including at least one of extrudates, spheres, flakes, stars, or tablets, although others forms are possible. The contacting may occur at a temperature of from about 100° C. to about 280° C., a pressure of from about 0 to about 1000 psia, and at a LHSV of from about 0.1 to about 10, although other conditions outside these ranges are possible. In one embodiment, the contacting occurs at temperature of from about 100° C. to about 240° C. In another embodiment, the contacting occurs at a pressure of from about 80 to about 500 psia.

In yet another respect, this invention is a process for continuous preparation of methyl tertiary butyl ether from tertiary butyl alcohol and methanol, including the step of continuously charging a tertiary butyl alcohol charge stock including from about 0.5 to about 2 wt. % formate impurities to a decomposition reactor containing a decomposition catalyst including at least one of rhodium, platinum, palladium, or a mixture thereof, and decomposing the formate impurities therein to form a tertiary butyl alcohol feedstock. The method also includes the step of continuously charging a reaction feed mixture including methanol and the tertiary butyl alcohol feedstock to an etherification reactor containing a bed of an etherification catalyst and reacting the reaction feed mixture therein to form a etherification reaction product including unreacted methanol, unreacted tertiary butyl alcohol, water, isobutylene and methyl tertiary butyl ether. Also included are the steps of continuously charging the etherification reaction product to a first methyl tertiary butyl ether distillation column and separating it therein into a first lighter distillation fraction including isobutylene, methanol and methyl tertiary butyl ether and a second heavier distillation fraction including methanol, tertiary butyl alcohol and water; continuously charging the first lighter distillation fraction to a methyl tertiary butyl ether processing zone for the formation of additional methyl tertiary butyl ether from the methanol and isobutylene contained therein and for the recovery of methyl tertiary butyl ether; continuously charging the second distillation fraction to a tertiary butyl alcohol recovery distillation column and separating it therein into a lower boiling tertiary butyl alcohol recycle fraction and a higher boiling water fraction; andcontinuously recycling the lower boiling tertiary butyl alcohol recycle fraction to the etherification reactor. In another typical embodiment, the catalyst may include palladium, the tertiary butyl alcohol feedstock from the decomposition reactor may have a tertiary butyl formate content of about 0.1 wt. % or less, and the tertiary butyl alcohol feedstock from the decomposition reactor may have a titratable acidity of about 3.0 mg KOH/g or less. However, tertiary butyl alcohol feedstocks having a tertiary butyl formate content of about 0.2 wt. % or less or a tertiary butyl formate content of about 0.3 wt. % or less, are also possible. In addition, the reaction conditions in the decomposition reactor may include a temperature of from about 100° C. to about 280° C., a pressure of from about 0 to about 1000 psia, and a flow rate of from about 0.1 to about 20 volumes of charge stock per reactor volume per hour. The catalyst in the decomposition reactor may be a palladium catalyst including an alumina support having from about 0.1 to about 1 wt. % of palladium deposited thereon. In one more typical embodiment, the catalyst in the decomposition reactor is a pre-reduced palladium catalyst including an alumina support having from about 0.1 to about 1 wt. % of palladium deposited thereon, and the method further includes the step of adding hydrogen to the tertiary butyl alcohol charge stock. In such an embodiment hydrogen is typically added in an amount sufficient so that the tertiary butyl alcohol charge stock includes from about 100 ppm to about 500 ppm hydrogen in the charge stock on a weight basis, although amounts of hydrogen may be added so that the tertiary butyl alcohol charge stock includes less than about 100 ppm or greater than about 500 ppm hydrogen in the charge stock on a weight basis, as well. Advantageously, in some embodiments, the tertiary butyl alcohol charge stock may further include one or more peroxides, and the method may further include the step of decomposing at least a portion of the peroxides in the decomposition reactor to form the tertiary butyl alcohol feedstock.

In embodiments of the disclosed, catalysts are provided for removing (or converting or decomposing) greater than about 50%, more typically greater than about 60%, even more typically greater than about 70%, even more typically greater than about 80%, even more typically greater than about 85%, even more typically greater than about 90%, and most typically greater than about 95% of formate esters contained within a charge stream or other mixture, such as an alcohol or tertiary butyl alcohol charge stream or mixture. However, conversions of less than about 50% of formate esters are also possible. Typically, such conversion or removal of formate esters (and/or simultaneous conversion or removal of peroxides) from a charge stream or mixture serves to reduce the acidity of the stream or mixture.

Although in some embodiments described herein, decontaminated alcohol or other charge streams typically comprise less than about 0.3% formate ester content, more typically less than about 0.2% formate ester content, and most typically less than about 0.1% formate ester content, it will be understood with benfit of this disclosure that benefit of the disclosed method may be achieved where decontaminated alcohol or other charge streams comprise greater than or equal to about 0.3% formate ester content as well.

DESCRIPTION OF ILLUSTRATIVE EMBODIMENTS

The disclosed method relates to the decomposition of esters, peroxides, and other impurities. More specifically, the disclosed method relates to the removal of formate esters, particularly t-butyl formate, from alcohol mixtures such as crude aqueous t-butanol charge stocks by passage over supported decomposition catalysts comprising at least one of rhodium, palladium, platinum, or mixtures thereof. Surprisingly, it has been found that the catalyst materials of the disclosed method are particularly effective at accomplishing formate ester removal. For example, the disclosed catalyst materials may provide greater than about 50%, more typically greater than about 60%, even more typically greater than about 70%, even more typically greater than about 80%, even more typically greater than about 90% and in some cases greater than about 95% t-butyl formate decomposition or removal, although benefits of the disclosed method may be realized at removal amounts of less than or equal to 50% as well. This is particularly true because removal or decomposition of formate esters and other acidic impurities in amounts greater or less than about 50% serves to reduce the amount of caustic or other basic material required to deacidify an effluent stream.

Figure 2:
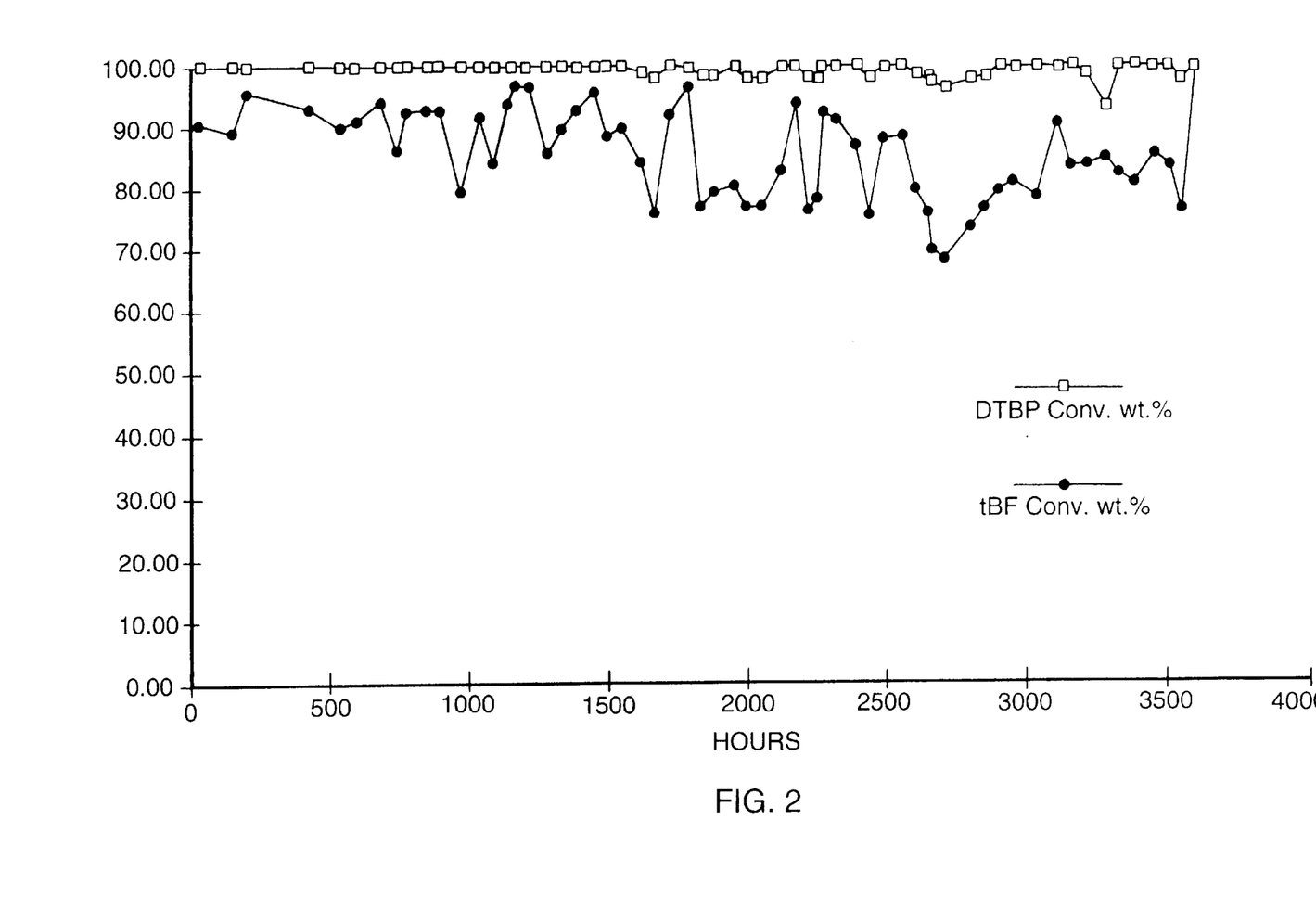
FIG. 2 illustrates decomposition of tertiary butyl formate and ditertiary butyl peroxide as a function of time according to one embodiment of the disclosed method employing a palladium catalyst.

More particularly, platinum-on-basic alumina catalyst may provide greater than about 95% t-butyl formate removal at about 180° C., and palladium-on-alumina catalyst may give greater than about 80% t-butyl formate decompositions at about 180° C. over an extended period of time, such as greater than about 3000 hours on stream as illustrated in FIG. 2 and Table 13.

Significantly, removal of formate esters, particularly t-butyl formate and methyl formate, is accomplished without the use of added caustic to lower the effluent acidity. Unexpectedly, alcohol streams (such as t-butanol streams) having relatively low acidity after formate removal may be achieved using the disclosed method. Furthermore, simultaneous removal of multiple impurities may be accomplished, including simultaneous removal of formate esters (such as t-butyl formate and/or methyl formate) and peroxides (such as di-t-butyl peroxide and/or allyl t-butyl peroxide).

It will be understood with benefit of the present disclosure that a decomposition catalyst of the disclosed method may be used under a variety of conditions and to purify a variety of compounds. For example, a decomposition catalyst may be utilized to purify any alcohol, mixture of alcohols, and/or aqueous alcohol mixtures contaminated with oxygenated impurities, such as esters and peroxides. In this regard, the term "alcohol mixture" as used herein means an alcohol, mixture of alcohols, and/or aqueous mixture of one or more alcohols. Furthermore, as used herein "contaminated with impurities" means that an alcohol or alcohol mixture contains one or more non-alcohol components or impurities (typically oxygen-containing components) that may be removed or decomposed by one or more of the disclosed decomposition catalysts. In this regard, a contaminated alcohol or alcohol mixture may also optionally include one or more impurities that may not be decomposed by the disclosed decomposition catalysts, for example acetic acid, and its homologues, etc. Benefits of the disclosed method may be realized in the presence or absence of these latter impurities. A "purified alcohol mixture" is used herein to mean an alcohol mixture that has had at least a portion of one or more non-alcohol components contained therein removed or decomposed by one or more of the disclosed decomposition catalysts.

Specific examples of alcohols or alcohol mixtures that may be purified using decomposition catalysts of the disclosed method include, but are not limited to, C-1 to C-20 aliphatic alcohols, and most typically tert-butyl alcohol. Examples of types of esters that may be removed include, but are not limited to, formate esters, orthoformate esters, etc. Specific esters that may be removed include, but are not limited to, tertiary butyl formate, methyl formate, tertiary amyl formate, etc. Examples of types of peroxide impurities that may be removed from alcohols include, but are not limited to, primary, secondary and tertiary aliphatic peroxides and hydroperoxides, etc. Specific peroxides that may be removed include, but are not limited to, tertiary butyl hydroperoxide, ditertiary butyl peroxide, allyl tertiary butyl peroxide, methyl tertiary butyl peroxide, etc. Most typically, liquid alcohol streams including formate esters are treated using the disclosed method.

Furthermore, it will be understood with benefit of this disclosure that decomposition catalysts of the disclosed method may be utilized in heterogeneous or homogenous catalysis operations and/or with or without supports in any suitable type of process in which an alcohol may be purified including, but not limited to, continuous or batch processes. More specifically, for example, said supported catalysts may utilize Group III and Group IV oxides plus carbon. In addition, decomposition catalysts of the disclosed method may be employed with a variety of types, shapes and sizes of supports including, but not limited to, pellets, extrudates, rings, granules, tablets, stars spheres, granules, chips etc.

A further advantage offered by decomposition catalysts of the present invention employing rhodium, platinum or palladium, and especially palladium is good decomposition performance (such as good conversion percentages and catalyst life), at relatively low cost.

Although optional, the disclosed decomposition catalysts may also comprise platinum, palladium and/or rhodium in combination with other metals, such as nickel.

Continuous Preparation of Methyl Tertiary Butyl Ether

In accordance with one typical embodiment of the disclosed method, a method for the continuous preparation of methyl tertiary butyl ether (MTBE) from tertiary butyl alcohol (tBA) and methanol (MeOH) is provided comprising the steps of:

a) continuously charging a tertiary butyl alcohol charge stock contaminated with from about 0.5 to about 10 wt. % of impurities, including peroxides and formates (and typically from about 0.1 wt. % to about 5 wt. formate esters) to a decomposition reactor containing a decomposition catalyst and substantially completely decomposing the formates therein to form a non-corrosive tertiary butyl alcohol feedstock having an acidity of 3.0 mg. KOH/g or less comprising tertiary butyl alcohol and isobutylene that is substantially completely free from peroxide and formate contaminants, wherein the decomposition catalyst comprises at least one of rhodium, platinum, palladium, or a mixture thereof, b) continuously charging a reaction feed mixture comprising methanol and the non-corrosive tertiary butyl alcohol feedstock to an etherification reactor containing a bed of an etherification catalyst and reacting said reaction feed mixture therein to form a non-corrosive etherification reaction product comprising unreacted methanol, unreacted tertiary butyl alcohol, water, isobutylene and methyl tertiary butyl ether, c) continuously charging the etherification reaction product to a first methyl tertiary butyl ether distillation zone and separating it therein into a first lighter distillation fraction comprising isobutylene, methanol and methyl tertiary butyl ether and a second heavier distillation fraction comprising methanol, tertiary butyl alcohol and water, d) continuously charging the first lighter distillation fraction to a methyl tertiary butyl ether processing zone for the formation of additional methyl tertiary butyl ether from the methanol and isobutylene contained therein and for the recovery of methyl tertiary butyl ether, and e) continuously charging the second distillation fraction to a tertiary butyl alcohol recovery distillation zone and separating it therein into a lower boiling tertiary butyl alcohol recycle fraction and a higher boiling water fraction.

Peroxide Decomposition

Tertiary butyl alcohol may be prepared by the thermal or catalytic decomposition of tertiary butyl hydroperoxide. It is also known to prepare tertiary butyl alcohol by the catalytic reaction of tertiary butyl hydroperoxide with propylene to form propylene oxide and tertiary butyl alcohol. A tertiary butyl alcohol charge stock derived from tertiary butyl hydroperoxide in this manner is typically contaminated with oxygen-containing impurities. A typical charge stock prepared in this fashion typically contains from about 90 to 99 wt. % of tertiary butyl alcohol and about 0.1 to about 10 wt. % of oxygen-containing contaminants including tertiary butyl hydroperoxide, ditertiary butyl peroxide acetone, methyl formate, tertiary butyl formate, isopropyl alcohol, dimethyl ether, etc.

In accordance with one embodiment of the disclosed method, a tertiary butyl alcohol charge stock containing formate and/or contaminants is typically fed to a decomposition reactor containing a bed of a decomposition catalyst where the contaminants are substantially completely catalytically decomposed. The decomposition catalyst typically comprises alumina (including basic alumina) or carbon having from about 0.01 to about 5 wt. % of rhodium, platinum, palladium or a mixture thereof deposited thereon, although other support materials for these catalyst materials (such as titania, zirconia, silica, silica-alumina, nickel on silica-alumina, clay, brick etc.) are also possible, as well as mixtures thereof. Typical reaction conditions include a temperature of about 100° C. to about 280° C., a pressure of about 0 to about 1000 psia at a flow rate of about 0.1 to 20 volumes of charge stock per reactor volume per hour to provide a tertiary butyl alcohol feedstock substantially completely free from oxygen-containing impurities. More typically, reaction temperatures should be in the range of from about 110° C. to about 240° C. However, reaction temperatures may be any temperature at which the disclosed catalyst compositions are capable of achieving decomposition of formate or peroxide impurities.

An effluent stream from an oxygenates-decomposition reactor typically comprises about 90 to about 99 wt. % of a mixture of tertiary butyl alcohol with isobutylene and typically contains less than about 0.3%, more typically less than about 0.2%, and most typically less than about 0.1 wt. % of formate contaminants.

The Oxygenates-Decomposition Catalyst

The oxygenates-decomposition catalyst to be used in accordance with the disclosed method is typically a supported decomposition catalyst consisting essentially of alumina or carbon having from about 0.01 to about10 wt. %, more typically from about 0.01 to about 5 wt. %, more typically from about 0.01 to about 1 wt. %, more typically from about 0.1% to about 1 wt. %, and most typically from about 0.1 to about 0.5 wt. % of at least one of rhodium, platinum, palladium, or a mixture thereof deposited thereon. However, it will be understood with benefit of this disclosure that any other wt. % of such catalyst materials suitable for purification of alcohols and decomposition of formate esters and/or peroxides may be employed. In one embodiment employing Rhodium alone, from about 0.1 to about 1 wt. % of Rhodium catalyst is most typically deposited on a support. In another embodiment employing Palladium alone, from about 0.1 to about 1 wt. %, and more typically from about 0.1 to about 0.5 wt. % Palladium catalyst is deposited on a support. The catalyst may of any suitable form for decomposition of impurities mentioned herein, including as a powder or in formed into extrudates, flakes, pellets, spheres, etc. Typically the catalyst is in the form of extrudates, more typically in the form of a catalyst-on-alumina extrudates, even more typically in the form of palladium-on-alumina extrudates. In the latter case, extrudates may be of any size, although extrudates of from about $\frac{1}{16}$" have been typically employed in experimental runs.

The Etherification Reaction Catalyst

In accordance with one embodiment of the disclosed method involving the manufacture of MTBE, an etherification reactor containing a bed of etherification catalyst is typically utilized. A typical catalyst is a sulfonic acid resin etherification catalyst such as a sulfonated polystyrene resin cross-linked with divinyl benzene.

Any suitable solid resin etherification catalyst may be used for this purpose, such as a strongly acidic ion exchange resin consisting essentially of sulfonated polystyrene. such as a divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalyst of this nature is disclosed, for example, in Rao U.S. Pat. No. 4,144,138.

Also, Kieselguhr impregnated with phosphoric acid as disclosed in Frolich U.S. Pat. No. 2,282,469, titania having phosphoric acid impregnated thereon as disclosed in Knifton U.S. Pat. No. 4,822,921, a heteropoly acid such as 12-tungstophosphoric acid or 12-molybdophosphoric acid supported on titania, etc., may be used.

Zeolites as disclosed in Japanese Patent 0007432 or aluminosilicate zeolites such as those disclosed in Chang et al. U.S. Pat. No. 4,058,576 may also be used.

The reaction conditions to be utilized when reacting methanol with tertiary butyl alcohol in the presence of a sulfonic acid resin etherification catalyst of the type disclosed in the related art include a reaction temperature of about 90° C. to about 140° C., a pressure of about 30 to about 500 psia and a space velocity of about 0.5 to about 20 volumes of feed per volume of etherification catalyst per hour.

Figure 1:
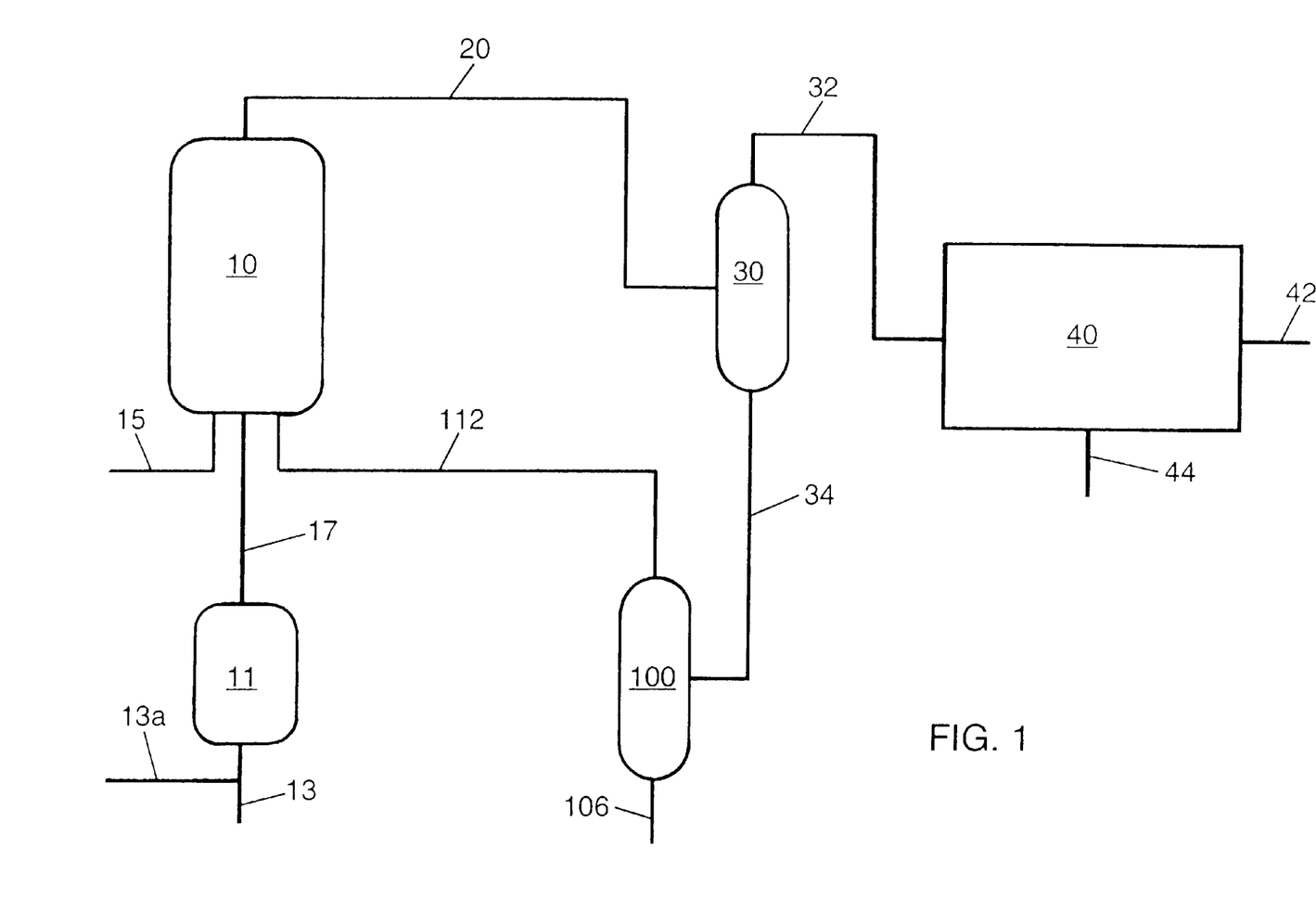
FIG. 1 is a schematic flow sheet with conventional parts omitted showing the general reaction and recovery sequence of the disclosed method for the manufacture and purification of methyl tertiary butyl ether.

Turning now to FIG. 1, there is shown a schematic flow sheet illustrating a typical method for the practice of the process of the disclosed method. In the drawing, conventional parts, such as valves, pumps, temperature control sensors, pressure sensors, heaters, coolers, flow control regulation apparatus, reflux condenses, reboilers, etc., have been omitted.

In accordance with the present embodiment, a tertiary butyl alcohol charge stock which is contaminated with formate impurities is initially charged by way of a tertiary butyl alcohol charge line 13 to a decomposition reactor 11, containing a bed of a decomposition catalyst typically comprising alumina or carbon typically having from about 0.01 to about 10 wt. %, more typically from about 0.01 to about 5 wt. %, and most typically from about 0.01 to about 1 wt. %, of rhodium, platinum, palladium, or a mixture thereof deposited thereon, which is operated at a temperature of about 100° C. to about 280° C., a pressure of about 0 to about 1000 psia and a flow rate of about 0.1 to 20 volumes of feedstock per reactor volume per hour to thereby provide a water-containing tertiary butyl alcohol reaction product comprising a mixture of tertiary butyl alcohol and isobutylene that is substantially free from formate contaminants.

The substantially oxygenates-free tertiary butyl alcohol reaction product is continuously discharged from the oxygenates decomposition reactor 11 by a discharge line 17 leading to an etherification reactor 10. Fresh methanol is continuously charged to etherification reactor 10 by a line 15, as is a recycle stream 112 containing recycle methanol and recycle tertiary butyl alcohol. The flow of methanol and tertiary butyl alcohol to the etherification reactor 10 through the lines 15, 17 and 112 is regulated so that a molar excess of methanol is present in the etherification reactor 10, such as, tor example, a molar ratio of about 1.1 to about 3 moles of methanol per mol. equivalent of tertiary butyl alcohol and isobutylene.

The etherification reactor 10 contains a bed of solid etherification catalyst. Any suitable etherification catalyst may be used such as, for example, a solid resin etherification of the type described above, such as a strongly acidic ion exchange resin consisting essentially of sulfonated polystyrene crosslinked with divinyl benzene (e.g., Dowex 50, Nalcite HCR, Amberlyst 15, etc.). As another example, the catalyst may be a fluorophosphoric acid-on-titania catalyst of the type disclosed in Knifton et al. U.S. Pat. No. 4,822,921 or a heteropoly acid such as 12-tungstophosphoric acid or 12-molybdophosphoric acid supported on an inert support such as titania.

Within the etherification reactor 10, the feed mixture is brought into contact with the bed of an etherification catalyst, such as a sulfonic acid resin etherification catalyst under reaction conditions including a pressure of about 30 to about 500 psia, and more typically from about 200 to about 300 psia, a temperature of about 30° C. to about 200° C., and more typically from about 80° C. to about 140° C., and still more typically from about 90° C. to about 130° C. When the catalyst is a supported phosphorus acid-type catalyst, the reaction temperature may suitably be in the range of about 150° C. to about 190° C.

Contact time within the etherification reactor is suitably such that about 0.5 to about 20 volumes of feed mixture per volume of etherification catalyst per hour are fed to the etherification reactor 10 and, more typically from about 1 to about 4 volumes of feed mixture per volume of etherification catalyst per hour.

Within the etherification reactor 10, methanol will exothermically react with the tertiary butyl alcohol and isobutylene to form methyl tertiary butyl ether which will be contained in a reaction product discharged from the etherification reaction zone 10 by way of a line 20 leading to a first methyl tertiary butyl ether (MTBE) distillation zone 30.

The etherification reaction product is charged to the first MTBE distillation zone 30 by way the charge line 20 and is fractionated therein under distillation conditions including a liquid reflux temperature of about 30° C. to about 100° C., and more typically about 40° C. to about 80° C., a reboiler temperature of about 80° C. to about 115° C., and more typically from about 95° C. to about 105° C., and a pressure of about 15 to about 60 psia, the distillation condition being selected such that substantially all of the MTBE in the etherification reaction product 20 is taken overhead from the first distillation zone 30 by a line 32. As a consequence, the first distillation fraction 32 taken overhead from the distillation zone 30 will comprise substantially all of the isobutylene and substantially all of the methyl tertiary butyl ether and some of the methanol charged to the first distillation zone 30. The second heavier distillation fraction 34 discharged from the first MTBE distillation zone 34 will comprise methanol, tertiary butyl alcohol and water.

The first lighter distillation fraction 32 is continuously charged to a methyl tertiary butyl ether processing zone 40 for the formation of additional methyl tertiary butyl ether from the methanol and isobutylene contained therein and for the recovery of methyl tertiary butyl ether. The methyl tertiary butyl ether is discharged from the methyl tertiary butyl ether processing zone 40 by a line 42 and other reaction products and by-products are discharged by a representative line 44.

The second distillation fraction 34 discharged from the first MTBE distillation column 30 is charged to a second tertiary butyl alcohol recovery distillation zone 100 where it is fractionated into a lower boiling distillation fraction discharged in the second distillation zone 100 by a line 112 leading to etherification reactor 10 and a higher boiling distillation fraction comprising water that is discharged from the distillation zone 100 by a line 106.

OPERATION

In accordance with a typical embodiment of the disclosed method, a tertiary butyl alcohol charge stock containing from about 90 to 99 wt. % of tertiary butyl alcohol and about 0.5 to about 10 wt. % of oxygen-containing contaminants including tertiary butyl hydroperoxide, ditertiary butyl peroxide, acetone, methyl formate, tertiary butyl formate, isopropyl alcohol, dimethyl ether, etc., is charged by a line 13 to a decomposition reactor 11 containing a supported decomposition catalyst consisting essentially of alumina or carbon having about 0.01 to about 10 wt. %, more typically from about 0.01 to about 5 wt. %, and most typically from about 0.01 to about 1 wt. %, of rhodium, platinum, palladium, or a mixture thereof deposited thereon. A separate hydrogen feed line 13a may be provided for adding or charging hydrogen to the charge stock, typically in an amount sufficient to form a feed stream typically containing from about 50 ppm to about 2000 ppm hydrogen, more typically from about 100 ppm to about 1000 ppm hydrogen, and most typically about 300 ppm, in the liquid charge stock on a weight basis. It will be understood with benefit of this disclosure that hydrogen may be added to create charge stocks having less than about 50 ppm and more than about 2000 ppm hydrogen in the liquid charge stock on a weight basis as well. Furthermore, hydrogen may be introduced in any other suitable manner, including directly into the reactor, such as by sparging. Hydrogen may be added in this manner, for example, when reduced or pre-reduced catalysts are employed, to enhance catalytic activity. In this regard, the disclosed catalysts may be reduced using any suitable method known in the art including, but not limited to, passing hydrogen gas over a catalyst at a temperature of from about 25° C. to about 250° C. It will be understood with benefit of this disclosure that benefits may be realized by adding hydrogen to a charge stock other than the above-described tertiary butyl alcohol charge stock and/or by employing reduced catalysts with other types of charge stocks, as well as any combination thereof with other configurations of process flow streams and equipment.

The charge stock is treated under decomposition conditions including a temperature of about 100° C. to about 280° C., a pressure of about 0 to about 1000 psia and a flow rate of about 0.1 to 20 volumes of fcedstock per reactor volume per hour to thereby provide a water-containing non-corrosive tertiary butyl alcohol reaction product feedstock comprising a mixture of tertiary butyl alcohol and isobutylene that is substantially free from formate contaminants and a titratable acidity of about 3.0 kg KOH/g or less, but more typically an acidity of about 1.5 mg KOH/g or less.

The feedstock is typically discharged from the oxygenates-decomposition reactor 11 by a line 17 leading to etherification reactor 10 containing a bed of a suitable etherification catalyst, such as Amberlyst 15 catalyst. Fresh methanol is continuously charged to etherification reactor 10 by a line 15, as is a recycle stream 112 containing recycle methanol and recycle tertiary butyl alcohol. The flow of methanol and tertiary butyl alcohol to the etherification reactor 10 through the lines 15, 17 and 112 is regulated so that a molar excess of methanol is present in the etherification reactor 10, such as, for example, a molar ratio of about 1.1 to about 3 moles of methanol per mol equivalent of tertiary butyl alcohol and isobutylene. Reaction conditions to be used in the etherification reactor 10 include a pressure of about 30 to about 500 psia, and more typically from about 200 to about 300 psia, a temperature of about 30° C. to about 200° C., and more typically from about 80° C. to about 140° C., and still more typically from about 90° C. to about 130° C. When the catalyst is a supported phosphorus acid-type catalyst, the reaction temperature may suitably be in the range of about 150° C. to about 190° C.

Contact time within the etherification reactor 10 is suitably such that about 0.5 to about 20 volumes of feed mixture per volume of etherification catalyst per hour are fed to the etherification reactor 10 and, more typically from about 1 to about 4 volumes of feed mixture per volume of etherification catalyst per hour.

The etherification reaction product is discharged from the reactor 10 by a line 20 leading to first methyl tertiary butyl ether distillation zone 30 where the reaction product 20 is separated into a lighter distillation fraction 32 containing isobutylene and methyl tertiary butyl ether and a second heavier fraction 34.

The first distillation fraction 32 is continuously charged to a methyl tertiary butyl ether processing zone 40 for the formation of additional methyl tertiary butyl ether from the methanol and isobutylene contained therein and for the recovery of methyl tertiary butyl ether. The methyl tertiary butyl ether is discharged from the methyl tertiary butyl ether processing zone 40 by a line 42 and other reaction products and by-products are discharged, as represented by a representative line 44.

The methyl tertiary butyl ether processing zone 40 may be operated in accordance with the manner known to those skilled in the art, as disclosed for example, is disclosed in Kruse et al. U.S. Pat. No. 5,243,091, Cassata et al. U.S. Pat. No. 5,395,982, Hwan et al. U.S. Pat. No. 5,354,912, etc.

The second distillation fraction 34 is discharged from the first MTBE distillation column 30 and is charged to a second tertiary butyl alcohol recovery distillation zone 100 where it is fractionated under distillation conditions including a liquid reflux temperature of about 35° C. to about 170° C., and more typically about 140° C. to about 150° C., and a reboiler temperature of about 100° C. to about 190° C., more typically about 170° C. to about 180° C., and at a pressure of about 15 to about 190 psia, and more typically about 110 to about 160 psia, into a lower boiling distillation fraction comprising tertiary butyl alcohol and methanol discharged in the second distillation zone 100 by a line 112 leading to etherification reactor 10 and a higher boiling distillation fraction comprising water that is discharged from the distillation zone 100 by a line 106.

EXAMPLES

The invention will be further illustrated by the following specific examples which are given by way of illustration, and not as a limitation on the scope of this invention. Where parts are mentioned, they are parts by weight.

Comparative Example A

This example illustrates the removal of formate esters from a crude aqueous tertiary butyl alcohol stream in the absence of a decomposition catalyst of the disclosed method.

To a 300 cc. capacity, upflow, continuous reactor constructed of stainless steel and having the necessary temperature, pressure and feed controls was charged a crude aqueous feedstock mixture containing tertiary butyl formate (TBF) and methyl formate (MF), as well as significant quantities of acetone ($AC_2O$), isopropanol (IPA) and methyl ethyl ketone (MEK). Temperature in the unit was maintained in the range of 180° C.–280° C. The unit pressure was 300 psi. Under steady state conditions, the effluent product was collected in steel bombs and analyzed by both glc techniques and for acidity. Typical results are summarized in Table 1, where the principal designations are: tertiary butyl formate, TBF; methyl formate, MF; tertiary butanol, tBA; acetone, $AC_2O$; isopropyl alcohol, IPA, methyl ethyl ketone, MEK; dimethyl ether, DME; and isobutylene, $C_4H_8$.

TABLE 1

ALKYL FORMATE DESTRUCTION
(Run 7288-79)

| Temp ° C. | LHSV | Sample | $H_2O$ | $C_4H_8$ | $AC_2O$ | IPA | tBA | MEK | DME | MF | tBF | tBF Conv. (%) | Acidity mg KOH/g |
|---|---|---|---|---|---|---|---|---|---|---|---|---|---|
|  |  | F-1 | 1.9 | 0.1 | 0.4 | 1.4 | 92.7 | 0.4 |  | 0.01 | 0.85 | — | 1.0 |
| 180 | 1.0 | 1 | 1.9 | 0.4 | 2.5 | 0.3 | 90.6 | 0.2 | 0.2 | 0.02 | 0.43 | 50 | 3.7 |
| 200 |  | 2 | 1.6 | 0.7 | 2.5 | 0.3 | 92.3 | 0.2 | 0.1 | 0.03 | 0.41 | 52 | 4.8 |
| 220 |  | 3 | 1.8 | 2.8 | 2.6 | 0.3 | 90.2 | 0.4 | 0.1 | 0.05 | 0.17 | 80 | 7.3 |
| 240 |  | 4 | 1.5 | 0.6 | 2.5 | 0.2 | 93.2 | 0.2 | 0.1 | 0.02 | 0.22 | 74 | 5.3 |
| 260 |  | 5 | 2.0 | 0.4 | 2.1 | 0.3 | 92.0 | 0.1 |  | 0.01 | 0.40 | 53 | 5.8 |
|  |  | F-2 | 1.7 | 0.1 | 1.6 | 0.3 | 92.8 | 0.1 |  | 0.01 | 0.86 | — | 1.3 |
| 280 |  | 6 | 2.0 | 0.5 | 2.7 | 0.3 | 90.8 | 0.1 |  | 0.01 | 0.41 |  | 3.4 |

Example 1

Alkyl Formate Decomposition Using Rhodium-on-Alumina Catalyst

This example illustrates the removal of formate esters from a crude aqueous tertiary butyl alcohol stream in the presence of a rhodium-on-alumina catalyst.

To the 300 cc. capacity, upflow, continuous reactor of comparative Example A was charged 100 cc. of a 0.5 wt. % rhodium-on-alumina catalyst as 1/16" extrudates. The catalyst was held in the central part of the unit using glass wool packing material. The crude aqueous feedstock mixture of Example A was charged to the reactor while the temperature in the unit was maintained in the range of 180° C.–240° C. The unit pressure was 300 psi. Under steady state conditions, the effluent product was collected in steel bombs and analyzed by both glc techniques and for acidity. Typical results are summarized in Table 2.

TABLE 2

ALKYL FORMATE DESTRUCTION
(Run 7288-85; Catalyst: 0.5% Rh/Al$_2$O$_3$)

| Temp (C.) | LHSV | Sample | H$_2$O | C$_4$H$_8$ | AC$_2$O/IPA | tBA | DME | MF | tBF | tBF Conv. (%) | Acidity mg KOH/g |
|---|---|---|---|---|---|---|---|---|---|---|---|
| | | F-1 | 2.0 | | 1.8 | 92.7 | | −.01 | 0.92 | — | 1.4 |
| 180 | 1.0[a] | 1 | 1.8 | 1.1 | 2.9 | 91.3 | 0.1 | 0.04 | 0.42 | 54 | 5.2 |
| 200 | | 2 | 2.3 | 3.8 | 3.0 | 87.6 | 0.1 | 0.02 | 0.24 | 74 | 5.5 |
| | | F-2 | 1.9 | 1.3 | 1.6 | 93.8 | | | 0.75 | — | 0.8 |
| 220 | | 3 | 1.8 | 3.6 | 2.7 | 89.3 | 0.1 | 0.01 | 0.08 | 89 | 3.8 |
| 240 | | 4 | 2.2 | 5.9 | 2.6 | 86.8 | 0.2 | 0.02 | 0.06 | 92 | 3.0 |

[a]Basis Reactor Volume

Example 2
Alkyl Formate Decomposition Using Rhodium-on-Carbon Catalyst

This example illustrates the removal of formate esters from a crude aqueous tertiary butyl alcohol stream in the presence of a rhodium-on-carbon catalyst.

Following the procedure of Example 1, the 300 cc. capacity reactor was charged with 100 cc. of a 0.5 wt. % rhodium-on-carbon catalyst, in flake form. The catalyst was held in the central part of the unit using glass wool packing material. The crude aqueous feedstock mixture of Example A was charged to the reactor while the temperature in the unit was maintained in the range of 100° C.–240° C. Under steady state conditions, the effluent product was collected in steel bombs and analyzed by both glc techniques and for acidity. Typical results are summarized in Table 3.

Example 3
Alkyl Formate Decomposition Using Rhodium-on-Alumina Catalyst

This example illustrates the removal of formate esters from a crude aqueous tertiary butyl alcohol stream in the presence of a rhodium-on-alumina catalyst.

To a 100 cc. capacity, upflow continuous reactor fitted with temperature, pressure and flow controls was charged 100 cc. of 0.5 wt. % rhodium-on-alumina catalyst as $\frac{1}{16}$" diameter extrudates, used previously for alkyl formate decomposition as illustrated in Example 1. The crude aqueous feedstock mixture of Example A was charged to the reactor while the temperature in the unit was maintained in the range of 180° C.–240° C. Under steady state conditions, the effluent product was collected in steel bombs and analyzed by both glc techniques and for acidity. Typical results are summarized in Table 4.

TABLE 3

ALKYL FORMATE DESTRUCTION
(Run 7288-84; Catalyst: 0.5% Rh/C)

| Temp (C.) | LHSV | Sample | H$_2$O | C$_4$H$_8$ | AC$_2$O/IPA | tBA | DME | MF | tBF | tBF Conv. (%) | Acidity mg KOH/g |
|---|---|---|---|---|---|---|---|---|---|---|---|
| | | F-1 | 1.9 | | 1.8 | 93.2 | | 0.01 | 0.86 | — | 1.2 |
| 100 | 0.17[a] | 1 | 2.0 | | 1.8 | 93.1 | | 0.01 | 0.84 | 2 | 1.0 |
| 120 | | 2 | 1.8 | | 1.9 | 93.2 | | 0.01 | 0.83 | 3 | 1.5 |
| 150 | | 3 | 2.1 | 1.6 | 2.3 | 91.6 | 0.1 | 0.01 | 0.53 | 38 | 2.5 |
| 175 | | 4 | 3.5 | 8.0 | 2.7 | 83.8 | 1.1 | 0.01 | 0.10 | 88 | 3.0 |
| 200 | | 5 | 4.4 | 13.5 | 2.7 | 76.6 | 1.8 | 0.02 | 0.02 | 98 | 3.1 |
| 220 | | 6 | 4.1 | 11.8 | 2.8 | 76.3 | 3.1 | 0.03 | 0.02 | 98 | 4.8 |
| 240 | | 7 | 5.7 | 23.2 | 2.5 | 65.3 | 3.9 | 0.09 | 0.01 | 99 | 2.9 |

[a]Basis Reactor Volume

TABLE 4

ALKYL FORMATE DESTRUCTION
(Run 7288-87; Catalyst: 0.5% Rh/Al$_2$O$_3$[a])

| Temp (C.) | LHSV | Sample | H$_2$O | C$_4$H$_8$ | AC$_2$O/IPA | tBA | DME | MF | tBF | tBF Conv. (%) | Acidity mg KOH/g |
|---|---|---|---|---|---|---|---|---|---|---|---|
|  |  | F-1 | 1.1 |  | 1.6 | 94.8 |  |  | 0.72 | — | 0.5 |
| 180 | 1.0[b] | 1 | 1.6 | 3.0 | 2.6 | 90.9 |  | 0.04 | 0.16 | 88 | 3.5 |
| 200 |  | 2 | 3.6 | 5.2 | 2.3 | 87.0 | 0.1 | 0.04 | 0.02 | 97 | 3.0 |
| 220 |  | 3 | 4.4 | 16.5 | 2.4 | 75.1 | 0.7 | 0.05 | 0.05 | 93 | 1.2 |
| 240 |  | 4 | 8.8 | 41.2 | 2.1 | 46.0 | 1.5 | 0.06 | 0.03 | 96 | 1.4 |

[a]Used Catalyst from Run 7288-85, 1/16" E, 100 cc
[b]Run in 100 cc Capacity Unit Examples 4 and 5

Alkyl Formate Decomposition Using Rhodium-on-Alumina Catalyst

These examples illustrate the removal of formate esters from a crude aqueous tertiary butyl alcohol stream in the presence of a rhodium-on-alumina catalyst.

Using the procedures and equipment of Example 3, removal of formate esters was confirmed using a 0.5 wt. % rhodium-on-alumina catalyst in spherical form (Example 4) and with a 0.5 wt. % rhodium-on-alumina catalyst in 1/8" diameter tablet form (Example 5). The results are summarized in Tables 5 and 6, respectively.

A review of the foregoing Example A and Examples 1 through 5 supports the following conclusions.

1. Comparative Example A illustrates some destruction of the tertiary butyl formate contained in the crude aqueous feed stream in the absence of a catalyst at the observed temperatures. However, the ester removal is accompanied by a sharp increase in effluent acidity. (See Table 1, samples 3 and 4.)

2. Example 1 confirms the use of 0.5 wt. % rhodium-on-alumina catalyst to remove more than 90 wt. % of the tertiary butyl formate from the crude aqueous feed stream while providing effluent streams alter treatment with acidities of 3.0 mg. KOH/g. (See Table 2, sample 4 at 240° C.)

TABLE 5

ALKYL FORMATE DESTRUCTION
(Run 7288-96; Catalyst: 0.5% Rh/Al$_2$O$_3$)

| Temp (C.) | LHSV | Sample | H$_2$O | C$_4$H$_8$ | AC$_2$O/IPA | tBA | DME | MF | tBF | tBF Conv. (%) | Acidity mg KOH/g |
|---|---|---|---|---|---|---|---|---|---|---|---|
|  |  | F-1 | 1.0 |  | 1.4 | 95.3 |  | 0.02 | 0.54 | — | 3.8 |
| 180 | 1.0 | 1 | 1.9 | 3.6 | 2.4 | 89.8 | 0.2 | 0.05 | 0.08 | 85 | 4.8 |
| 200 |  | 2 | 3.3 | 8.8 | 2.4 | 83.1 | 0.7 | 0.08 | 0.02 | 96 | 3.4 |
| 220 |  | 3 | 5.9 | 25.5 | 2.2 | 63.4 | 1.4 | 0.14 | 0.02 | 96 | 2.2 |
| 240 |  | 4 | 9.3 | 36.7 | 2.2 | 49.6 | 1.9 | 0.13 | 0.02 | 96 | 2.0 |

TABLE 6

ALKYL FORMATE DESTRUCTION
(Run 7288-97; Catalyst: 0.5% Rh/Al$_2$O$_3$)

| Temp (C.) | LHSV | Sample | H$_2$O | C$_4$H$_8$ | AC$_2$O/IPA | tBA | DME | MF | tBF | tBF Conv. (%) | Acidity mg KOH/g |
|---|---|---|---|---|---|---|---|---|---|---|---|
|  |  | F-1 | 0.5 | 0.1 | 1.4 | 95.4 |  | 0.03 | 0.58 | — | 3.8 |
| 180 | 1.0 | 1 | 2.4 | 6.2 | 1.3 | 86.7 | 0.1 | 9.06 | 0.18 | 69 | 4.4 |
| 200 |  | 2 | 7.6 | 15.4 | 2.3 | 71.7 |  | 0.10 | 0.02 | 97 | 4.0 |
| 220 |  | 3 | 5.7 | 23.6 | 2.4 | 66.2 | 0.4 | 0.11 | 0.01 | 98 | 2.0 |
|  |  | F-2 | 1.2 | 0.1 | 1.5 | 94.6 |  | 0.01 | 0.60 | — | 0.90 |
| 240 |  | 4 | 5.6 | 26.8 | 2.2 | 60.1 | 0.5 | 0.09 | 0.03 | 95 | 2.0 |

3. Example 2 illustrates a similar result with a 0.5 wt. % rhodium-on-graphite.

4. Example 3 shows the performance of the same quantity of a 0.5 wt. % rhodium-on-alumina catalyst in a smaller capacity unit with greater than 95 wt. % is removal of tertiary butyl formate and effluent acidity of only 1.2 mg. KOH/g. at 220 to 240° C. (See Table 4, samples 3 and 4.)

5. Examples 4 and 5 confirm the use of other rhodium-on-alumina catalysts in spherical and tablet form where more than 98 wt. % of the tertiary butyl formate is removed from the crude aqueous feed stream.

Example 6

Alkyl Formate Decomposition Using Palladium-on-Carbon Catalyst

This example illustrates the removal of formate esters from a crude aqueous tbutanol stream in the presence of a palladium-on-carbon catalyst.

To a 100 cc capacity, upflow, continuous reactor fitted with temperature, pressure and flow controls, was charged 100 cc of 5.0% palladium-on-carbon granular catalyst. The crude aqueous t-butanol feedstock mixture containing t-butyl formate ("TBF"), as well as significant quantities of acetone ("AC$_2$O"), isopropanol ("IPA"), and methyl ethyl ketone ("MEK"), was charged to said reactor, while the temperature was maintained in the 140–220° C. range. Under steady state conditions, the effluent product was collected in stainless steel bombs and analyzed by both glc techniques and for acidity plus SAP #.

Typical results are summarized in Table 7.

Example 7

Alkyl Formate Decomposition Using Palladium-on-Carbon Catalyst

This example illustrates removal of formate esters from crude t-butanol using another palladium catalyst.

Following the procedures and using the equipment of Example 6, removal of formate esters was confirmed using a 0.5% palladium-on-carbon, granular catalyst. The results are summarized in Table 8.

TABLE 8

ALKYL FORMATE DESTRUCTION
(Run 7393-10; Catalyst: 5% Pd/C$^{a,b}$)

| Temp | | | | | glc Analyses (wt. %) | | | | | tBF | Acidity | SAP # |
|---|---|---|---|---|---|---|---|---|---|---|---|---|
| (° C.) | LHSV | Sample | H$_2$O | C$_4$H$_8$ | AC$_2$O/IPA | tBA | DME | MF | tBF | Conv. (%) | (mg KOH/g) | (mg KOH/g) |
|  |  | F-1 | 2.1 | 0.1 | 1.6 | 93.3 |  |  | 0.61 | — | 0.5 | 7.7 |
| 140 | 1.0 | 1 | 2.9 |  | 1.6 | 92.4 |  | 0.01 | 0.58 | 5 | 1.1 | 7.8 |
| 160 |  | 2 | 1.8 | 0.3 | 2.0 | 93.1 |  | 0.03 | 0.52 | 15 | 1.1 | 6.6 |
| 180 |  | 3 | 2.1 | 2.9 | 2.2 | 89.9 | 0.2 | 0.05 | 0.39 | 36 | 1.6 | 6.7 |
| 200 |  | 4 | 3.1 | 8.5 | 3.4 | 80.6 | 0.6 | 0.06 | 0.22 | 64 | 2.0 | 4.3 |
| 220 |  | 5 | 3.6 | 10.7 | 2.4 | 81.1 | 0.7 | 0.10 | 0.14 | 77 | 1.6 | 3.1 |

$^a$Granules, 100 cc
$^b$Reduction at room temperature in stream of H$_2$, overnight Examples 8 and 9

Alkyl Formate Decomposition Using Other Palladium Catalysts Over Extended Periods These examples illustrate the removal of formate esters from crude t-butanol using palladium-supported catalysts over extended periods.

Following the procedures and using the equipment of Example 6, removal of formate esters, as well as di-t-butyl peroxide ("DTBP") and allyl t-butyl peroxide ("ATBP") was confirmed using the following solid catalysts:

For Example 8(Table 9): 0.5% palladium-on-alumina, ⅛" diameter spheres.

For Example 9 (Table 10): 0.5% palladium-on-carbon, granules.

Test conditions in both cases were at a temperature=180° C., pressure=500 psi pressure, and LHSV=1.0. Each test was allowed to continue for 500+ hours. The results are summarized in Tables 9 and 10, respectively.

TABLE 7

ALKYL FORMATE DESTRUCTION
(Run 7393-7; Catalyst: 5% Pd/C$^{a,b}$)

| Temp | | | | | glc Analyses (wt. %) | | | | tBF | Acidity | SAP # |
|---|---|---|---|---|---|---|---|---|---|---|---|
| (° C.) | LHSV | Sample | H$_2$O | C$_4$H$_8$ | AC$_2$O/IPA | DME | MF | tBF | Conv. (%) | (mg KOH/g) | (mg KOH/g) |
|  |  | F-1 | 1.4 | 0.1 | 1.6 | 94.3 |  | 0.58 | — | 0.4 | 7.3 |
| 140 | 1.0 | 1 | 1.5 | 0.2 | 1.6 | 93.5 | 0.01 | 0.54 | 7 | 1.4 | 6.9 |
| 160 |  | 2 | 1.7 | 1.6 | 2.1 | 92.0 | 0.1 | 0.02 | 0.42 | 28 | 1.6 | 6.2 |
| 180 |  | 3 | 2.2 | 3.6 | 2.3 | 89.8 | 0.5 | 0.04 | 0.23 | 60 | 1.8 | 5.4 |
| 200 |  | 4 | 3.2 | 8.5 | 2.3 | 83.5 | 0.9 | 0.05 | 0.09 | 83 | 2.3 | 3.5 |
| 220 |  | 5 | 4.0 | 13.3 | 2.1 | 77.8 | 1.3 | 0.06 | 0.02 | 97 | 2.2 | 2.6 |

$^a$Granules, 100 cc
$^b$Reduced at room temperature in stream of H$_2$, overnight

TABLE 9

ALKYL FORMATE DESTRUCTION
(Run 7393-11; Catalyst: 0.5% Pd/Al$_2$O$_3$[a])

| Temp (°C.) | LHSV | Sample | Time (hr) | H$_2$O | C$_4$H$_8$ | AC$_2$O/ IPA | tBA | MTBE | MEK | DME | MF | tBF |
|---|---|---|---|---|---|---|---|---|---|---|---|---|
| | | | | | | | | glc Analyses (wt. %) | | | | |
| | | F-1 | | 1.3 | 0.1 | 1.5 | 94.3 | | 0.2 | | | 0.60 |
| 180 | 1.0 | 1 | 24 | 10.7 | 3.5 | 1.6 | 79.6 | 1.4 | 0.4 | 0.2 | 0.01 | 0.02 |
| | | 2 | 72 | 2.5 | 4.1 | 2.0 | 89.3 | 0.3 | 0.5 | 0.1 | 0.02 | 0.05 |
| | | 3 | 147 | 2.6 | 6.3 | 2.1 | 86.4 | 0.5 | 0.5 | 0.2 | 0.02 | 0.03 |
| | | 4 | 192 | 1.7 | 4.2 | 2.2 | 90.4 | 0.2 | 0.5 | 0.1 | 0.02 | 0.05 |
| | | F-2 | | 1.4 | 0.2 | 1.6 | 94.1 | | 0.3 | | | 0.60 |
| | | 5 | 312 | 3.3 | 5.7 | 2.3 | 86.0 | 0.4 | 0.5 | 0.2 | 0.02 | 0.03 |
| | | 6 | 360 | 1.6 | 2.9 | 2.4 | 90.3 | 0.1 | 0.5 | 0.1 | 0.02 | 0.13 |
| | | 7 | 528 | 1.6 | 1.7 | 2.2 | 92.9 | | 0.5 | 0.1 | | 0.01 |
| | | 8 | 624 | 1.3 | 1.9 | 2.4 | 92.2 | | 0.5 | 0.1 | 0.02 | 0.12 |
| | | 9 | 672 | 1.3 | 2.4 | 2.5 | 91.7 | | 0.5 | 0.1 | | 0.09 |

| Temp (°C.) | LHSV | Sample | tBF Conv. (%) | DTBP | DTBF Conv. (%) | ATBP | ATBP Conv. (%) | Acidity (mg/KOH/g) | SAP # (mg/KOH/g) |
|---|---|---|---|---|---|---|---|---|---|
| | | | | glc Analyses (wt. %) | | | | | |
| | | F-1 | — | 0.75 | — | 0.74 | — | 0.5 | 7.7 |
| 180 | 1.0 | 1 | 97 | 0.01 | 99 | 0.02 | 97 | 2.5 | 2.5 |
| | | 2 | 92 | 0.02 | 97 | 0.02 | 97 | 3.5 | 1.8 |
| | | 3 | 95 | 0.01 | 99 | 0.02 | 97 | 3.5 | 1.9 |
| | | 4 | 92 | 0.02 | 97 | 0.02 | 97 | 2.9 | 1.6 |
| | | F-2 | — | 0.74 | — | 0.74 | — | 0.9 | 7.9 |
| | | 5 | 95 | 0.01 | 99 | 0.02 | 97 | 2.4 | 2.2 |
| | | 6 | 88 | 0.02 | 97 | 0.01 | 99 | 2.8 | 4.0 |
| | | 7 | 98 | 0.01 | 99 | 0.01 | 99 | 3.1 | 3.8 |
| | | 8 | 80 | 0.01 | 99 | 0.01 | 99 | 2.9 | 2.4 |
| | | 9 | 85 | 0.01 | 99 | 0.01 | 99 | 3.7 | 4.0 |

[a]1/8 Spheres, 100 cc

TABLE 10

ALKYL FORMATE DESTRUCTION
(Run 7393-15; Catalyst: 0.5% Pd/C[a])

| Temp (°C.) | LHSV | Sample | Time (hr) | H$_2$O | C$_4$H$_8$ | AC$_2$O/ IPA | tBA | MEK | DME | MF | tBF |
|---|---|---|---|---|---|---|---|---|---|---|---|
| | | | | | | glc Analyses (wt. %) | | | | | |
| | | F-1 | | 1.4 | | 1.4 | 94.6 | 0.2 | | | 0.59 |
| 180 | 1.0 | 1 | 48 | 1.8 | 1.8 | 2.2 | 91.7 | 0.2 | | 0.06 | 0.40 |
| | | 2 | 93 | 1.7 | 1.3 | 2.3 | 92.5 | 0.2 | | 0.07 | 0.45 |
| | | F-2 | | 1.3 | | 1.5 | 94.7 | 0.2 | | | 0.60 |
| | | 3 | 165 | 1.6 | 0.5 | 2.0 | 93.3 | 0.1 | | 0.05 | 0.49 |
| | | 4 | 310 | 4.4 | 0.2 | 2.3 | 90.6 | 0.4 | | | 0.51 |
| | | 5 | 454 | 1.3 | | 2.3 | 93.4 | 0.3 | | | 0.52 |
| | | 6 | 573 | 1.8 | | 2.3 | 93.2 | 0.3 | | 0.02 | 0.51 |

| Temp (°C.) | LHSV | Sample | tBF Conv. (%) | DTBP | DTBF Conv. (%) | ATBP | ATBP Conv. (%) | Acidity (mg/KOH/g) | SAP # (mg/KOH/g) |
|---|---|---|---|---|---|---|---|---|---|
| | | | | glc Analyses (wt. %) | | | | | |
| | | F-1 | — | 0.74 | — | 0.73 | — | 0.3 | 8.2 |
| 180 | 1.0 | 1 | 32 | 0.05 | 93 | 0.02 | 97 | [b] | 7.8 |
| | | 2 | 24 | 0.05 | 93 | 0.03 | 96 | 1.4 | 7.6 |
| | | F-2 | — | 0.74 | — | 0.01 | — | 0.3 | 8.2 |
| | | 3 | 18 | 0.05 | 93 | 0.02 | — | [c] | [c] |
| | | 4 | 15 | 0.00 | 100 | 0.02 | — | 1.0 | 6.6 |
| | | 5 | 13 | 0.06 | 92 | 0.01 | — | 1.1 | 7.3 |
| | | 6 | 15 | 0.06 | 92 | 0.01 | — | [b] | [b] |

[a]Granules, 100 cc
[b]Insufficient Sample
[c]Analysis Not Available

Example 10
Alkyl Formate Decomposition Using a Platinum-on-Alumina Catalyst

This Example illustrates removal of formate esters from crude t-butanol using a platinum-supported catalyst.

Following the procedures and using the equipment of Example 6, removal of formate esters was confirmed with the aid of 0.25% platinum-on-basic alumina, 7–8 mm diameter spherical catalyst. Typical analytical data are summarized in Table 11.

TABLE 11

ALKYL FORMATE DESTRUCTION
(Run 7288-92; Catalyst: 0.25% Pt/Al$_2$O$_3$[a,b])

| Temp (° C.) | LHSV | Sample | H$_2$O | C$_4$H$_8$ | AC$_2$O/IPA | tBA | DME | MF | tBF | tBF Conv. (%) | Acidity (mg KOH/g) |
|---|---|---|---|---|---|---|---|---|---|---|---|
|  |  | F-1 | 1.1 |  | 1.5 | 95.1 |  | 0.02 | 0.59 | — | 3.8 |
| 180 | 1.0 | 1 | 1.2 | 0.8 | 2.1 | 93.3 |  | 0.02 | 0.03 | 95 | 5.4 |
| 200 |  | 2 | 1.9 | 2.8 | 2.3 | 91.2 | 0.1 | 0.03 | 0.01 | 98 | 4.3 |
| 220 |  | 3 | 3.0 | 10.3 | 2.0 | 82.2 | 0.1 | 0.06 | 0.01 | 98 | 3.1 |
| 240 |  | 4 | 4.9 | 18.5 | 2.4 | 72.1 | 0.2 | 0.07 | 0.01 | 98 | 2.6 |

[a]7–8 Mesh spheres, 100 cc
[b]Reduced at 400° C. in stream of H$_2$, overnight

A review of the forgoing Examples 6–11 supports the following conclusions:

1. Example 6 confirms the use of a 5% palladium-on-carbon catalyst to remove >96% of t-butyl formate from crude aqueous t-butanol feed stream with a typical effluent acidity (after treatment) of 2.2 mg KOH/g and a SAP # of 2.6 mg KOH/g at 220° C. (see Table 7, sample 5).

2. Example 7 serves to show that a 0.5% palladium-on-carbon catalyst (Table 8) is also effective at achieving t-butyl formate destruction over the temperature range 140–220° C.

3. Examples 8 and 9 illustrate the life characteristics of selected embodiments of palladium-on-alumina and palladium-on-carbon catalysts at 180° C. Simultaneous removal of t-butyl formate, di-t-butyl peroxide ("DIBP") and allyl t-butyl peroxide ("ATBP") has been demonstrated with these catalysts under the specified conditions. Particularly effective in long term service is the 0.5% palladium-on-alumina spheres (Example 8) in which TBF decomposition levels of >80% have been maintained in this experimental series over 650+ hours on stream. The 0.5% palladium-on-carbon embodiment (Example 9) exhibited TBF decomposition below 40% throughout the run (see Table 10).

4. Example 10 serves to demonstrate the removal of t-butyl formate using a platinum-on-basic alumina catalyst. Here, 95% t-butyl formate removal is achieved at 180° C. (see Table 11, sample 1).

Examples 11–28
Alkyl Formate Decomposition Using Various Platinum and Palladium Catalysts Following procedures and equipment similar to that used in Example 6 and using catalyst charged to a 100 cc or 300 cc reactor, removal of formates and peroxides was confirmed using a variety of platinum and palladium catalysts.

Example 11

TABLE 12

ALKYL FORMATE DESTRUCTION
(Run 7393-25; Catalyst:
Engelhard 0.5% Pd on Al$_2$O$_3$ -- approx. ⅛" Stars)

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| F-1 | — | 0.64 | 0 | 0.66 | — | 0.46 |
| 120 | 182–188 | 0.012 | 98 | 0.016 | 98 | 3.72 |
| 696 | 181–188 | 0.020 | 97 | 0.016 | 98 | 2.89 |
| 1032 | 182–190 | 0.124 | 81 | 0.032 | 95 | 2.46 |
| 1232 | 180–190 | 0.116 | 82 | 0.022 | 97 | 2.86 |
| 1316 | 178–191 | 0.033 | 95 | 0 | 100 | 1.79 |
| 1520 | 189–198 | 0.083 | 87 | 0 | 100 | 0.80 |
| 1776 | 152–192 | 0.138 | 79 | 0 | 100 | 2.50 |
| 2088 | 184–197 | 0.054 | 92 | 0 | 100 | 2.16 |

In Example 11 (Table 12), a 0.5% palladium-on-alumina catalyst in the form of approximately ⅛" stars was used to simultaneously degrade tBF and DTBP at a LHSV of 3.0. A review of the data of Example 11 (Table 12) shows that there was only a minor loss in activity of the catalyst after almost 2100 hours of on-stream time at a space velocity of 3.0.

Example 12

TABLE 13

ALKYL FORMATE DESTRUCTION
(Run 7393-37; Catalyst: Engelhard 0.3% Pd on Al$_2$O$_3$ -- 1/16" extrudates)

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| F-1 | — | 0.643 | 0 | 0.603 | 0 | 0.71 |
| 24 | 170–181 | 0.061 | 91 | 0 | 100 | 2.06 |
| 192 | 176–187 | 0.028 | 96 | 0 | 100 | 3.63 |
| 528 | 181–192 | 0.063 | 90 | 0 | 100 | 1.79 |
| 729 | 174–186 | 0.089 | 86 | 0 | 100 | 1.45 |
| 839 | 183–190 | 0.046 | 93 | 0 | 100 | 1.27 |

TABLE 13-continued

ALKYL FORMATE DESTRUCTION
(Run 7393-37; Catalyst: Engelhard 0.3% Pd on $Al_2O_3$ -- 1/16" extrudates)

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| 1032 | 175–186 | 0.053 | 92 | 0 | 100 | 0.81 |
| 1128 | 183–191 | 0.038 | 94 | 0 | 100 | 0.25 |
| 1268 | 183–195 | 0.091 | 86 | 0 | 100 | 1.24 |
| 1436 | 182–187 | 0.027 | 96 | 0 | 100 | 1.40 |
| 1604 | 176–185 | 0.102 | 84 | 0.007 | 99 | 1.85 |
| 1772 | 183–191 | 0.021 | 97 | 0 | 100 | 1.89 |
| 1940 | 179–189 | 0.126 | 80 | 0 | 100 | 1.23 |
| 2108 | 173–179 | 0.112 | 83 | 0 | 100 | 1.29 |
| 2228 | 177–187 | 0.142 | 78 | 0.012 | 98 | 1.47 |
| 2302 | 178–186 | 0.055 | 91 | 0 | 100 | 1.40 |
| 2374 | 174–179 | 0.083 | 87 | 0 | 100 | 1.58 |
| 2542 | 175–182 | 0.074 | 88 | 0 | 100 | 1.79 |
| 2651 | 170–180 | 0.194 | 70 | 0.017 | 97 | 1.15 |
| 2839 | 182–190 | 0.149 | 77 | 0.011 | 98 | 1.43 |
| 3023 | 175–185 | 0.138 | 79 | 0 | 100 | 2.07 |
| 3359 | 173–180 | 0.121 | 81 | 0 | 100 | 1.58 |
| 3528 | 175–183 | 0.148 | 77 | 0.013 | 98 | n.d. |

In Example 12 (Table 13), a 0.3% palladium-on-alumina catalyst in the form of 1/16" extrudates was used to simultaneously decompose tBF and DTBP at a LHSV of 3.0. A review of the data of Example 12 (Table 13) shows that there was only a minor loss in activity of the catalyst after more than 3500 hours of on-stream time at a space velocity of 3.0. To further illustrate this characteristic, tBF and DTBP conversion percentages are plotted versus time in FIG. 2.

Example 13

TABLE 14

ALKYL FORMATE DESTRUCTION
(Run 7393-38; Catalyst: 0.3% Pd on basic $Al_2O_3$ -- 1/16" extrudates)

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| F-1 |  | 0.643 |  | 0.603 |  | 1.12 |
| 24 | 182–184 | 0.264 | 59 | 0.313 | 48 | 2.34 |
| 48 | 177–186 | 0.265 | 59 | 0.422 | 30 | 4.28 |
| 336 | 179–180 | 0.340 | 47 | 0.162 | 73 | 1.78 |
| 384 | 184–185 | 0.336 | 48 | 0.268 | 56 | 2.42 |
| 432 | 177–180 | 0.399 | 38 | 0.416 | 31 | 1.80 |

In Example 13 (Table 14), a 0.3% palladium-on-basic alumina catalyst in the form of 1/16" extrudates was used to simultaneously decompose tBF and DTBP at a LHSV of 3.0.

Example 14

TABLE 15

ALKYL FORMATE DESTRUCTION
(Run 7393-34; Catalyst:
Engelhard .5% Pd/$Al_2O_3$ -- approx. 1/8" Spheres)

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| F-1 |  | 0.636 |  | 0.649 |  | — |
| 23 | 183 | 0.129 | 80 | 0.041 | 94 | — |
| 91 | 183 | 0.133 | 79 | 0.033 | 95 | — |
| 122 | 182 | 0.138 | 78 | 0.035 | 95 | — |
| 145 | 183 | 0.146 | 77 | 0.042 | 94 | — |
| 172 | 184 | 0.145 | 77 | 0.039 | 94 | — |
| 194 | 183 | 0.146 | 77 | 0.037 | 94 | — |
| 259 | 182–183 | 0.149 | 77 | 0.040 | 94 | — |

In Example 14 (Table 15), a 0.5% palladium-on-alumina catalyst in the form of approximately 1/8" spheres was used to simultaneously decompose tBF and DTBP at a LHSV of 3.0. A review of the data of Example 14 (Table 15) shows that 0.5% palladium on alumina spheres is satisfactory for the removal of TBF and DTBP.

Example 15

TABLE 16

ALKYL FORMATE DESTRUCTION
(Run 7393-39; Catalyst: Engelhard .1% Pd/$Al_2O_3$ -- approx. 1/8" Stars)

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| F-1 |  | 0.705 |  | 0.713 |  | 0.48 |
| 25 | 179–181 | 0.373 | 47 | 0.154 | 78 | 0.91 |
| 95 | 179–180 | 0.358 | 49 | 0.046 | 94 | 0.53 |
| 190 | 179–180 | 0.374 | 47 | 0.165 | 77 | 0.81 |
| 262 | 178–180 | 0.324 | 54 | 0.122 | 83 | 1.51 |

In Example 15 (Table 16), a 0.1% palladium-on-alumina catalyst in the form of approximately 1/8" stars was used to simultaneously decompose tBF and DTBP at a LHSV of 3.0.

Example 16

TABLE 17

ALKYL FORMATE DESTRUCTION
(Run 7393-40; Catalyst: Engelhard .3% Pd/$Al_2O_3$ -- approx. 1/8" Stars)

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| F-1 | 0 | 0.663 |  | 0.675 |  | 0.63 |
| 30 | 197–198 | 0.156 | 76 | 0.055 | 92 | 1.94 |
| 53 | 175–176 | 0.277 | 58 | 0.216 | 68 | 2.51 |
| 77 | 181–182 | 0.294 | 56 | 0.254 | 62 | 1.38 |
| 119 | 184 | 0.292 | 56 | 0.224 | 67 | 1.47 |
| 143 | 175 | 0.296 | 55 | 0.221 | 67 | 1.75 |
| 197 | 165–166 | 0.381 | 43 | 0.381 | 44 | 1.56 |
| 226 | 180 | 0.283 | 57 | 0.224 | 67 | 1.69 |

In Example 16 (Table 17), a 0.3% palladium-on-alumina catalyst in the form of aproximately 1/8" stars was used to simultaneously decompose tBF and DTBP at a LHSV of 5.0.

Example 17

TABLE 18

ALKYL FORMATE DESTRUCTION
(Run 7393-43; Catalyst:
0.05% Pd on 12% Ni on silica-alumina -- 1/16" extrudates)

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| F-1 | | 0.663 | | 0.675 | | 0.63 |
| 6 | 181–186 | 0.389 | 41 | 0.133 | 80 | 1.67 |
| 26 | 183–184 | 0.411 | 38 | 0.126 | 81 | 1.89 |
| 54 | 170–175 | 0.420 | 37 | 0.126 | 81 | 1.55 |
| 72 | 171–180 | 0.421 | 37 | 0.124 | 82 | 1.44 |
| 94 | 177–178 | 0.434 | 35 | 0.140 | 79 | 1.64 |
| 118 | 172–180 | 0.430 | 35 | 0.134 | 80 | 1.56 |
| 142 | 170–177 | 0.324 | 51 | 0.046 | 93 | 1.70 |
| 169 | 177–181 | 0.318 | 52 | 0.032 | 95 | 1.61 |
| 245 | 173–184 | 0.304 | 54 | 0.027 | 96 | 1.53 |
| 264 | 174–184 | 0.302 | 54 | 0.032 | 95 | 1.72 |
| 293 | 165–175 | 0.307 | 54 | 0.035 | 95 | 1.60 |
| 312 | 174–184 | 0.250 | 62 | 0.000 | 100 | 1.58 |

In Example 17 (Table 18), a 0.5% palladium on 12% nickel on silica-alumina catalyst in the form of 1/16" extrudates was used to simultaneously decompose tBF and DTBP at a LHSV of 3.0. Nickel was observed to leach from the catalyst during the run.

Example 18

TABLE 19

ALKYL FORMATE DESTRUCTION
(Run 7393-42; Catalyst:
0.3% Pd on $Al_2O_3$ -- approx. 1/8" Spheres (Calsicat))

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| F-1 | | 0.667 | | 0.688 | | 0.65 |
| 24 | 180–184 | 0.196 | 71 | 0.000 | 100 | 1.26 |
| 45 | 172 | 0.215 | 68 | 0.000 | 100 | 2.08 |
| 117 | 178–184 | 0.226 | 67 | 0.000 | 100 | 1.40 |
| 168 | 173–177 | 0.310 | 54 | 0.011 | 98 | 1.41 |
| 213 | 177–181 | 0.339 | 50 | 0.020 | 97 | 0.96 |
| 309 | 181–188 | 0.298 | 56 | 0.000 | 100 | 1.31 |

In Example 18 (Table 19), a 0.3% palladium-on-alumina catalyst in the form of approximately 1/8" stars was used to simultaneously decompose tBF and DTBP at a LHSV of 3.0. A review of the data of Example 18 (Table 19) shows this catalyst is satisfactory as a formate-peroxide removal catalyst.

Example 19

TABLE 20

ALKYL FORMATE DESTRUCTION
(Run 7393-44; Catalyst: 0.05% Pd on 12% Ni on silica-alumina -- 1/16"
extrudates (UCl P8-7135) (Reduced with $H_2$ at 260° C.))

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| F-1 | | 0.666 | | 0.659 | | 0.55 |
| 24 | 157–193 | 0.189 | 72 | 0.000 | 100 | 1.64 |
| 186 | 168–196 | 0.071 | 89 | 0.000 | 100 | 1.81 |
| 386 | 169–189 | 0.062 | 91 | 0.000 | 100 | 0.20 |
| 570 | 164–192 | 0.221 | 67 | 0.000 | 100 | 1.45 |

TABLE 20-continued

ALKYL FORMATE DESTRUCTION
(Run 7393-44; Catalyst: 0.05% Pd on 12% Ni on silica-alumina -- 1/16"
extrudates (UCl P8-7135) (Reduced with $H_2$ at 260° C.))

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| 745 | 164–194 | 0.185 | 72 | 0.000 | 100 | 1.37 |
| 906 | 166–193 | 0.217 | 67 | 0.000 | 100 | 1.65 |

In Example 19 (Table 20), a reduced 0.05% palladium on 12% nickel on silicacatalyst alumina catalyst in the form of 1/16" extrudates was used to simultaneously decompose tBF and DTBP at a LHSV of 2.0. Nickel was leached from the catalyst during the run.

Example 20

TABLE 21

ALKYL FORMATE DESTRUCTION
(Run 7393-44; Catalyst: .05% Pd on 12% Ni on silica-alumina -- 1/16"
extrudates (SN-7618, 50% DHT-4A) (Reduced with $H_2$ at 260° C.))

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| F-1 | | 0.666 | | 0.659 | | 0.55 |
| 22 | 180 | 0.211 | 68 | 0.077 | 88 | 0.00 |
| 47 | 180 | 0.236 | 65 | 0.081 | 88 | 0.00 |
| 70 | 180 | 0.217 | 67 | 0.070 | 89 | 0.00 |
| 168 | 180–181 | 0.190 | 71 | 0.026 | 96 | 0.00 |
| 214 | 180 | 0.151 | 77 | 0.000 | 100 | 1.51 |
| 241 | 180–181 | 0.178 | 73 | 0.014 | 98 | 0.37 |
| 335 | 180 | 0.147 | 78 | 0.000 | 100 | 1.25 |

In Example 20 (Table 21), a reduced 0.5% palladium on 12% nickel on silica-alumina catalyst in the form of 1/16" extrudates was used to simultaneously decompose tBF and DTBP at a LHSV of 1.0. Nickel was observed to leach from the catalyst during the run.

Example 21

TABLE 22

ALKYL FORMATE DESTRUCTION
(Run 7393-46; Catalyst: 0.05% Pd on 12% Ni on silica-alumina -- 1/16"
extrudates (UCl PP-3242HT) (Reduced with $H_2$ at 260° C.))

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| F-1 | | 0.630 | | 0.629 | | 0.57 |
| 46 | 190–200 | 0.113 | 82 | 0.000 | 100 | 0.43 |
| 210 | 181–191 | 0.105 | 83 | 0.000 | 100 | 0.55 |
| 330 | 185–195 | 0.081 | 87 | 0.000 | 100 | 2.59 |
| 449 | 186–191 | 0.223 | 65 | 0.000 | 100 | 1.61 |
| 552 | 176–189 | 0.198 | 69 | 0.000 | 100 | 1.62 |
| 665 | 180–191 | 0.197 | 69 | 0.000 | 100 | 1.85 |
| 713 | 179–190 | 0.222 | 65 | 0.000 | 100 | 1.60 |

In Example 21 (Table 22), a reduced 0.05% palladium on 12% nickel on silica-alumina catalyst in the form of 1/16" extrudates was used to simultaneously decompose tBF and DTBP at a LHSV of 1.0. Nickel was leached from the catalyst during the run.

Example 22

TABLE 23

ALKYL FORMATE DESTRUCTION
(Run 7393-47; Catalyst:
0.5% Pd on $Al_2O_3$ -- approx. 1/8" Spheres (Calsicat))

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| F-1 |  | 0.647 |  | 0.634 |  | 0.84 |
| 45 | 184–198 | 0.193 | 70 | 0.007 | 99 | 1.82 |
| 114 | 189–196 | 0.128 | 80 | 0.000 | 100 | 1.27 |
| 162 | 190–196 | 0.137 | 79 | 0.000 | 100 | 1.18 |
| 210 | 188–197 | 0.121 | 81 | 0.000 | 100 | 0.23 |
| 283 | 187–197 | 0.128 | 80 | 0.000 | 100 | 0.29 |

In Example 22 (Table 23), a 0.5% palladium-on-alumina catalyst in the form of approximately 1/8" spheres was used to simultaneously decompose tBF and DTBP at a LHSV of 3.0. This catalyst did not appear to lose activity during the run.

Example 23

TABLE 24

ALKYL FORMATE DESTRUCTION
(Run 7393-48; Catalyst: 0.3% Pd on $Al_2O_3$ -- 1/16" extrudates
(Prereduced 24 hrs at 25° C., $H_2$ over feed tank))

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| F-1 |  | 0.666 |  | 0.398 |  | 0.83 |
| 25 | 181 | 0.014 | 98 | 0.023 | 94 | 2.33 |
| 60 | 181 | 0.030 | 96 | 0.026 | 93 | 2.03 |
| 108 | 181 | 0.028 | 96 | 0.029 | 93 | 1.31 |
| 163 | 180 | 0.028 | 96 | 0.000 | 100 | 1.05 |
| 230 | 181 | 0.040 | 94 | 0.028 | 93 | 1.35 |
| 284 | 180 | 0.059 | 91 | 0.022 | 94 | 1.89 |
| 308 | 180 | 0.066 | 90 | 0.026 | 93 | 0.00 |
| 379 | 181 | 0.069 | 90 | 0.028 | 93 | 0.00 |

In Example 23 (Table 24), a reduced 0.3% palladium-on-alumina catalyst in the form of 1/16" extrudates was used to simultaneously decompose tBF and DTBP at a LHSV of 3.0. The difference between this catalyst and the catalyst of Example 24 is that in this run, the catalyst was prereduced with hydrogen and a small amount of hydrogen kept on the feed tank. In this way, a small amount of (dissolved) hydrogen was fed to the catalyst along with the liquid feed. The catalyst did not appear to lose activity over the life of the run.

Example 24

TABLE 25

ALKYL FORMATE DESTRUCTION
(Run 7393-49; Catalyst: 0.3% Pd on $Al_2O_3$ -- 1/16" extrudates
(Not prereduced, no $H_2$ over feed tank))

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| F-1 |  | 0.674 |  | 0.397 |  | 0.37 |
| 25 | 179–180 | 0.116 | 83 | 0.105 | 74 | 1.67 |
| 60 | 179–180 | 0.148 | 78 | 0.116 | 71 | 1.58 |
| 108 | 181 | 0.125 | 81 | 0.071 | 82 | 2.80 |
| 163 | 181 | 0.122 | 82 | 0.000 | 100 | 1.52 |
| 230 | 181 | 0.134 | 80 | 0.081 | 80 | 2.15 |
| 284 | 181 | 0.111 | 84 | 0.045 | 89 | 2.23 |
| 308 | 181 | 0.120 | 82 | 0.046 | 88 | 0.00 |
| 379 | 181 | 0.115 | 83 | 0.046 | 88 | 0.00 |

In Example 24 (Table 25), a 0.3% palladium-on-alumina catalyst in the form of 1/16" extrudates was used to simultaneously decompose tBF and DTBP at a LHSV of 3.0.

Example 25

TABLE 26

ALKYL FORMATE DESTRUCTION
(Run 7393-35; Catalyst: Engelhard 0.3% $Pd/Al_2O_3$ -- 1/8" Tablets)

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| F-1 |  | 0.660 |  | 0.677 |  | 0.52 |
| F-2 |  | 0.000 |  | 0.000 |  | 0.51 |
| Avg. |  | 0.660 |  | 0.677 |  | 0.52 |
| 23 | 163–176 | 0.284 | 57 | 0.135 | 80 | 2.83 |
| 48 | 189–195 | 0.180 | 73 | 0.095 | 86 | 1.28 |
| 168 | 177–183 | 0.106 | 84 | 0.063 | 91 | 2.03 |
| 186 | 183–186 | 0.012 | 98 | 0.000 | 100 | 3.46 |
| 401 | 175–186 | 0.313 | 53 | 0.052 | 92 | 1.64 |
| 552 | 180–198 | 0.249 | 62 | 0.000 | 100 | 1.40 |
| 600 | 180–194 | 0.225 | 66 | 0.000 | 100 | 1.28 |
| 672 | 175–193 | 0.233 | 65 | 0.000 | 100 | 1.17 |
| 723 | 167–185 | 0.409 | 38 | 0.049 | 93 | 1.04 |
| 768 | 159–172 | 0.383 | 42 | 0.210 | 69 | 1.12 |
| 840 | 198–204 | 0.229 | 65 | 0.000 | 100 | 1.27 |

In Example 25 (Table 26), a 0.3% palladium-on-alumina catalyst in the form of 1/8" tablets was used to simultaneously decompose tBF and DTBP at a LIISV of 3.0. The catalyst may be compared to other catalyst forms with a higher surface area/packing density.

Example 26

TABLE 27

ALKYL FORMATE DESTRUCTION
(Run 7393-51; Catalyst: 0.3% Pd on $Al_2O_3$ -- 1/16" extrudates
Not prereduced, no $H_2$ over feed tank)

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| F-1 |  | 0.666 |  | 0.398 |  | 0.83 |
| 49 | 181 | 0.104 | 84 | 0.071 | 82 | 1.55 |
| 171 | 181 | 0.119 | 82 | 0.061 | 85 | 1.36 |
| 290 | 181 | 0.126 | 81 | 0.061 | 85 | 1.71 |
| 385 | 181 | 0.127 | 81 | 0.060 | 85 | 1.76 |
| 510 | 181 | 0.145 | 78 | 0.073 | 82 | 1.54 |
| 627 | 181 | 0.124 | 81 | 0.061 | 85 | 1.33 |
| 722 | 181 | 0.123 | 82 | 0.061 | 85 | 1.68 |
| 968 | 180 | 0.115 | 83 | 0.052 | 81 | 1.41 |
| 1060 | 180 | 0.131 | 80 | 0.000 | 100 | 1.46 |

In Example 26 (Table 27), a 0.3% palladium-on-alumina catalyst in the form of 1/16" extrudates was used to simultaneously decompose tBF and DTBP at a LHSV of 3.0. When the data of this example is compared with the data of Example 27 (Table 28), prereduction of the catalyst and a pad of hydrogen over the feed tank is seen to be beneficial in increasing conversion efficiency of tBF and DTBP.

Example 27

TABLE 28

ALKYL FORMATE DESTRUCTION
(Run 7393-50; Catalyst: 0.3% Pd Al$_2$O$_3$ -- 1/16" extrudates
(Prereduced with H$_2$ for 24 hrs at 25° C., H$_2$ over feed tank))

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| F-1 |  | 0.674 |  | 0.397 |  | 0.37 |
| 26 | 181 | 0.031 | 95 | 0.022 | 94 | 1.07 |
| 49 | 181 | 0.045 | 93 | 0.026 | 93 | 1.64 |
| 121 | 181 | 0.056 | 92 | 0.026 | 93 | 1.59 |
| 171 | 180 | 0.067 | 90 | 0.027 | 93 | 1.60 |
| 217 | 180 | 0.059 | 91 | 0.023 | 94 | 1.59 |
| 290 | 180 | 0.064 | 91 | 0.028 | 93 | 1.60 |
| 337 | 180 | 0.062 | 91 | 0.027 | 93 | 2.19 |
| 385 | 180 | 0.063 | 91 | 0.028 | 93 | 1.69 |
| 403 | 180–181 | 0.060 | 91 | 0.030 | 92 | 1.50 |
| 510 | 180 | 0.061 | 91 | 0.028 | 93 | 1.67 |
| 558 | 180 | 0.057 | 92 | 0.027 | 93 | 1.85 |
| 627 | 180 | 0.061 | 91 | 0.028 | 93 | 1.47 |
| 674 | 180 | 0.063 | 91 | 0.029 | 93 | 1.51 |
| 722 | 180 | 0.058 | 91 | 0.027 | 93 | 1.98 |
| 791 | 180 | 0.059 | 91 | 0.028 | 93 | 1.41 |
| 863 | 180 | 0.055 | 92 | 0.026 | 93 | 1.48 |
| 874 | 180 | 0.054 | 92 | 0.024 | 94 | 1.47 |
| 1010 | 180 | 0.065 | 90 | 0.028 | 93 | 1.96 |
| 1060 | 180 | 0.065 | 90 | 0.000 | 100 | 1.46 |

In Example 27 (Table 28), a 0.3% palladium-on-alumina catalyst in the form of 1/16" extrudates was used to simultaneously decompose tBF and DTBP at a LHSV of 3.0. As can be seen by the data in Table 28, prereduction of the catalyst with hydrogen, and mantaining a pad of hydrogen on the feed tank is seen to increase conversion efficiency of tBF and DTBP.

Example 28

TABLE 29

ALKYL FORMATE DESTRUCTION
(Run 7393-52; Catalyst:
0.3% Pd on Al$_2$O$_3$ -- approx. 1/8" Spheres (Calsicat))

| Time (Hr.) | Temp. (° C.) | tBF (Wt. %) | tBF Conv. (%) | DTBP (Wt. %) | DTBP Conv. (%) | Acid No. mgKOH/g |
|---|---|---|---|---|---|---|
| F-1 |  | 0.659 |  | 0.401 |  | 0.00 |
| 24 | 180 | 0.216 | 67 | 0.023 | 94 | 1.61 |
| 73 | 180 | 0.238 | 64 | 0.021 | 95 | 1.67 |
| 145 | 181 | 0.209 | 68 | 0.023 | 94 | 1.27 |
| 193 | 180–181 | 0.263 | 60 | 0.021 | 95 | 2.03 |
| 241 | 180 | 0.264 | 60 | 0.026 | 94 | 1.60 |
| 313 | 179–180 | 0.270 | 59 | 0.030 | 93 | 1.17 |
| 362 | 180 | 0.268 | 59 | 0.029 | 93 | 1.10 |
| 409 | 180 | 0.258 | 61 | 0.027 | 93 | 1.14 |
| 505 | 180 | 0.257 | 61 | 0.028 | 93 | 1.53 |

In Example 28 (Table 29), a 0.3% palladium-on-alumina catalyst in the form of approxumately 1/8" spheres was used to simultaneously decompose tBF and DTBP at a LHSV of 3.0.

While the invention may be adaptable to various modifications and alternative forms, specific embodiments have been shown by way of example and described herein. However, it should be understood that the invention is not intended to be limited to the particular forms disclosed. Rather, the invention is to cover all modifications, equivalents, and alternatives falling within the spirit and scope of the invention as defined by the appended claims. Moreover, the different aspects of the disclosed compositions and methods may be utilized in various combinations and/or independently. Thus the invention is not limited to only those combinations shown herein, but rather may include other combinations.

What is claimed is:

1. A process for decomposing esters, comprising contacting at least one formate ester with a catalyst comprising at least one of rhodium, platinum, palladium or a mixture thereof under conditions such that said formate ester is decomposed.

2. The process of claim 1, wherein said formate ester comprises tertiary butyl formate, methyl formate, or tertiary amyl formate.

3. The process of claim 1, wherein said formate ester comprises tertiary butyl formate.

4. The process of claim 3, wherein said formate ester is present in a contaminated alcohol mixture and said contacting comprises contacting said contaminated alcohol mixture with said catalyst; wherein said contaminated alcohol mixture further comprises at least one of a primary, secondary or tertiary aliphatic peroxide or hydroperoxide; and wherein said contacting further comprises contacting said alcohol mixture with said catalyst under conditions such that said peroxide is decomposed.

5. The process of claim 2, wherein said contacting occurs at a temperature of from about 100° C. to about 280° C., and at a pressure of from about 0 to about 1000 psia.

6. The process of claim 5, wherein said catalyst comprises a support having from about 0.01 wt. % to about 10 wt. % of platinum deposited thereon; and wherein said support comprises at least one of alumina, silica alumina, titania, zirconia, silica, nickel, carbon, or a mixture thereof.

7. The process of claim 5, wherein said catalyst comprises a support having from about 0.01 wt. % to about 10 wt. % of palladium deposited thereon; and wherein said support comprises at least one of alumina, silica alumina, titania, zirconia, silica, nickel, carbon, or a mixture thereof.

8. The process of claim 5, wherein said catalyst comprises a support having from about 0.01 wt. % to about 10 wt. % of rhodium deposited thereon; and wherein said support comprises at least one of alumina, silica alumina, titania, zirconia, silica, nickel, carbon, or a mixture thereof.

9. The process of claim 1, wherein said catalyst is a pre-reduced catalyst, and wherein said contacting further comprises contacting said ester with said catalyst in the presence of hydrogen.

10. A process for removing formate ester impurities from a contaminated alcohol mixture to form a purified alcohol mixture, comprising contacting said contaminated alcohol mixture with a catalyst material comprising at least one of rhodium, platinum, palladium, or a mixture thereof under conditions such that said formate ester impurities are decomposed and said alcohol mixture purified.

11. The process of claim 10, wherein said contaminated alcohol mixture comprises tertiary butyl alcohol.

12. The process of claim 11, wherein said contaminated alcohol mixture further comprises at least one of a primary, secondary or tertiary aliphatic peroxide or hydroperoxide, and wherein said contacting further comprises contacting said alcohol mixture with said catalyst under conditions such that said peroxide is decomposed.

13. The process of claim 11, wherein said catalyst material is pre-reduced, and wherein said contacting further comprises contacting said contaminated alcohol mixture with said catalyst material in the presence of hydrogen.

14. The process of claim 11, wherein said contaminated alcohol mixture comprises from about 0.1 wt. % to about 5 wt. % of formate ester impurities.

15. The process of claim 14, wherein said formate ester impurities comprise tertiary butyl formate, and wherein said purified alcohol mixture has a tertiary butyl formate content of about 0.1 wt. % or less.

16. The process of claim 11, wherein said purified alcohol mixture has a titratable acidity of about 3.0 mg KOH/g or less.

17. The process of claim 11, wherein said purified alcohol mixture has a titratable acidity of about 1.5 mg KOH/g or less.

18. The process of claim 14, wherein greater than about 50% of said formate ester impurities are decomposed.

19. The process of claim 14, wherein said catalyst comprises palladium, and wherein greater than about 90% of said formate ester impurities are removed from said contaminated alcohol mixture.

20. The process of claim 14, wherein said catalyst comprises palladium, and wherein said catalyst is effective to remove greater than about 50% of said formate ester impurities from said contaminated alcohol mixture over a period of greater than about 3000 hours.

21. The process of claim 14, wherein said catalyst comprises an alumina or carbon support having from about 0.1 wt. % to about 5 wt. % of platinum deposited thereon.

22. The process of claim 14, wherein said catalyst comprises an alumina or carbon support having from about 0.1 wt. % to about 5 wt. % of palladium deposited thereon.

23. The process of claim 14, wherein said catalyst comprises an alumina or carbon support having from about 0.1 wt. % to about 5 wt. % of rhodium deposited thereon.

24. The process of claim 22, wherein said support comprises alumina.

25. The process of claim 22, wherein said support comprises carbon.

26. The process of claim 22, wherein said palladium catalyst has a form comprising at least one of extrudates, spheres, flakes, stars, or tablets.

27. The process of claim 14, wherein said contacting occurs at a temperature of from about 100° C. to about 280° C., a pressure of from about 0 to about 1000 psia, and at a LHSV of from about 0.1 to about 10.

28. The process of claim 26, wherein said contacting occurs at temperature of from about 110° C. to about 240° C.

29. The process of claim 26, wherein said contacting occurs at a pressure of from about 80 to about 500 psia.

30. The process of claim 4, wherein said peroxide is tertiary butylhydroperoxide.

31. The process of claim 4, wherein said peroxide is tertiary butyl hydroperoxide, ditertiary butyl peroxide, allyl tertiary butyl peroxide, or methyl tertiary butyl hydroperoxide.

32. The process of claim 4, wherein said contaminated alcohol mixture comprises at least one aliphatic alcohol having from about 1 to about 20 carbon atoms.

33. The process of claim 4, wherein said contaminated alcohol mixture comprises at least one of tertiary butyl alcohol, methanol, isopropyl alcohol, or a mixture thereof.

34. The process of claim 4, wherein said contaminated alcohol mixture comprises tertiary butyl alcohol.

35. The process of claim 12, wherein said peroxide is tertiary butyl hydroperoxide, ditertiary butyl peroxide, allyl tertiary butyl peroxide, or methyl tertiary butyl peroxide.

36. The process of claim 12, wherein said peroxide is tertiary butylhydroperoxide.

37. A process for removing formate ester impurities from a contaminated alcohol mixture to form a purified alcohol mixture, comprising contacting said contaminated alcohol mixture with a catalyst material comprising at least one of rhodium, platinum, palladium, or a mixture thereof under conditions such that said formate ester impurities are decomposed and said alcohol mixture purified; wherein said formate ester impurities comprise tertiary butyl formate and wherein said contaminated alcohol mixture comprises tertiary butyl alcohol.

38. The process of claim 37, wherein said contaminated alcohol mixture further comprises peroxide; wherein said contacting further comprises contacting said alcohol mixture with said catalyst under conditions such that said peroxide is decomposed; and wherein said peroxide comprises tertiary butyl hydroperoxide, ditertiary butyl peroxide, allyl tertiary butyl peroxide, methyl tertiary butyl peroxide, or a mixture thereof.

39. The process of claim 1, wherein said catalyst comprises palladium.

40. The process of claim 37, wherein said catalyst comprises palladium.

* * * * *